United States Patent
Paris, III

(10) Patent No.: US 11,688,015 B2
(45) Date of Patent: *Jun. 27, 2023

(54) USING DE-IDENTIFIED HEALTHCARE DATA TO EVALUATE POST-HEALTHCARE FACILITY ENCOUNTER TREATMENT OUTCOMES

(71) Applicant: Vigilytics LLC, Victor, NY (US)

(72) Inventor: Andrew L. Paris, III, Victor, NY (US)

(73) Assignee: Vigilytics LLC, Victor, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/167,247

(22) Filed: Feb. 4, 2021

(65) Prior Publication Data

US 2021/0182428 A1 Jun. 17, 2021

Related U.S. Application Data

(63) Continuation of application No. 15/939,727, filed on Mar. 29, 2018, now Pat. No. 10,943,028, which is a
(Continued)

(51) Int. Cl.
*H04L 29/00* (2006.01)
*G06Q 40/08* (2012.01)
(Continued)

(52) U.S. Cl.
CPC ......... *G06Q 40/08* (2013.01); *G06F 21/6245* (2013.01); *G06F 21/6254* (2013.01);
(Continued)

(58) Field of Classification Search
CPC . G06Q 40/08; G06F 21/6245; G06F 21/6254; G16H 10/20; G16H 10/40;
(Continued)

(56) References Cited

U.S. PATENT DOCUMENTS

| 5,721,777 A | * | 2/1998 | Blaze | G06Q 20/4093 |
| | | | | 705/52 |
| 5,956,400 A | * | 9/1999 | Chaum | H04L 63/0407 |
| | | | | 707/999.009 |

(Continued)

FOREIGN PATENT DOCUMENTS

| CA | 2760773 | 11/2010 |
| WO | WO 2001/018631 | 3/2001 |

(Continued)

OTHER PUBLICATIONS

"Group," The American Heritage Dictionary, 2014 Houghton Mifflin Harcourt, Retrieved online: https://ahdictionary.com/word/search.html?q=group (accessed Oct. 23, 2014), 3 pages.
(Continued)

*Primary Examiner* — Don G Zhao
(74) *Attorney, Agent, or Firm* — Fish & Richardson P.C.

(57) ABSTRACT

A computer-implemented method includes producing medical information that characterizes a group of individuals from a set of private data representing pre or post-encounter characteristics of the individuals, wherein the individuals have had encounters with a healthcare facility. The identity of the individuals is unattainable from the produced medical information. The method also includes providing the produced medical information to report the pre or post-encounter characteristics of the group.

15 Claims, 7 Drawing Sheets

Related U.S. Application Data continuation of application No. 15/606,265, filed on May 26, 2017, now Pat. No. 9,965,651, which is a continuation of application No. 15/136,318, filed on Apr. 22, 2016, now Pat. No. 9,665,685, which is a continuation of application No. 14/082,433, filed on Nov. 18, 2013, now Pat. No. 9,323,892, which is a continuation-in-part of application No. 12/827,745, filed on Jun. 30, 2010, now Pat. No. 9,118,641.

(60) Provisional application No. 61/729,207, filed on Nov. 21, 2012, provisional application No. 61/222,428, filed on Jul. 1, 2009.

(51) Int. Cl.
  *G06F 21/62* (2013.01)
  *G16H 10/40* (2018.01)
  *G16H 50/70* (2018.01)
  *G16H 40/20* (2018.01)
  *G16H 10/20* (2018.01)
  *H04L 9/40* (2022.01)
  *G16H 70/60* (2018.01)
  *G16H 15/00* (2018.01)
  *G16H 10/60* (2018.01)

(52) U.S. Cl.
  CPC ............ *G16H 10/20* (2018.01); *G16H 10/40* (2018.01); *G16H 15/00* (2018.01); *G16H 40/20* (2018.01); *G16H 50/70* (2018.01); *G16H 70/60* (2018.01); *H04L 63/0428* (2013.01); *H04L 63/10* (2013.01); *H04L 63/102* (2013.01); *G16H 10/60* (2018.01)

(58) Field of Classification Search
  CPC ........ G16H 15/00; G16H 40/20; G16H 50/70; G16H 70/60; G16H 10/60; H04L 63/0428; H04L 63/10; H04L 63/102
  See application file for complete search history.

(56) References Cited

U.S. PATENT DOCUMENTS

| | | | |
|---|---|---|---|
| 6,302,844 B1* | 10/2001 | Walker | A61B 5/0022 600/300 |
| 6,874,085 B1* | 3/2005 | Koo | H04L 63/0428 713/182 |
| 6,947,561 B1* | 9/2005 | Faber | G06F 21/445 380/259 |
| 7,650,628 B2* | 1/2010 | Zimmerman | G06F 21/6245 726/2 |
| 7,716,487 B2* | 5/2010 | Venkatesan | G06F 21/10 380/278 |
| 7,900,245 B1* | 3/2011 | Geddes | H04L 63/0407 713/172 |
| 8,037,052 B2* | 10/2011 | Kariathungal | G06F 16/951 707/709 |
| 8,055,910 B2* | 11/2011 | Kocher | G06F 21/10 713/168 |
| 8,108,355 B2* | 1/2012 | Zhang | G06F 16/2272 707/711 |
| 8,126,734 B2* | 2/2012 | Dicks | G16H 40/67 710/16 |
| 8,131,566 B2* | 3/2012 | Dicks | A61N 1/37247 710/16 |
| 8,131,646 B2* | 3/2012 | Kocher | G11B 20/0021 380/231 |
| 8,229,742 B2* | 7/2012 | Zimmerman | G16Z 99/00 704/235 |
| 8,296,341 B2* | 10/2012 | Hagan | H04L 67/306 707/830 |
| 9,118,641 B1 | 8/2015 | Paris, III | |
| 9,141,758 B2 | 9/2015 | Kress et al. | |
| 9,323,892 B1 | 4/2016 | Paris, III | |
| 9,355,273 B2 | 5/2016 | Stevens et al. | |
| 9,633,223 B1* | 4/2017 | Blackwell, Jr. | G06F 21/602 |
| 9,665,685 B1* | 5/2017 | Paris, III | G16H 10/40 |
| 9,965,651 B1 | 5/2018 | Paris, III | |
| 10,109,375 B1 | 10/2018 | Paris, III | |
| 10,886,012 B1 | 1/2021 | Paris, III | |
| 10,943,028 B1* | 3/2021 | Paris, III | H04L 63/0428 |
| 2002/0016923 A1* | 2/2002 | Knaus | G16H 10/60 705/3 |
| 2002/0188869 A1* | 12/2002 | Patrick | G06F 21/6245 726/4 |
| 2003/0154405 A1* | 8/2003 | Harrison | H04L 63/123 726/9 |
| 2004/0078236 A1* | 4/2004 | Stoodley | G16H 70/20 705/2 |
| 2004/0143403 A1* | 7/2004 | Brandon | G16B 25/10 702/19 |
| 2004/0215981 A1 | 10/2004 | Ricciardi et al. | |
| 2005/0119941 A1* | 6/2005 | James | G06Q 10/10 705/2 |
| 2005/0177050 A1* | 8/2005 | Cohen | G16H 10/60 600/509 |
| 2005/0234739 A1 | 10/2005 | Schoenberg | |
| 2005/0261941 A1 | 11/2005 | Scarlat | |
| 2005/0267782 A1* | 12/2005 | Zahlmann | G16H 10/20 705/3 |
| 2006/0004772 A1* | 1/2006 | Hagan | G06Q 20/4014 |
| 2006/0020611 A1* | 1/2006 | Gilbert | G06F 21/6254 |
| 2006/0089857 A1* | 4/2006 | Zimmerman | G16Z 99/00 705/2 |
| 2006/0184524 A1* | 8/2006 | Pollanz | G16H 10/60 |
| 2006/0229919 A1 | 10/2006 | Pugh | |
| 2007/0033419 A1* | 2/2007 | Kocher | G11B 20/00086 713/193 |
| 2007/0043594 A1* | 2/2007 | Lavergne | G06Q 10/10 705/64 |
| 2007/0106752 A1* | 5/2007 | Moore | G06F 21/6254 709/217 |
| 2007/0106753 A1* | 5/2007 | Moore | G06Q 10/10 709/217 |
| 2007/0130465 A1* | 6/2007 | Zeng | H04L 63/0407 713/171 |
| 2007/0157297 A1* | 7/2007 | Patrick | G06F 21/6245 726/6 |
| 2007/0185737 A1* | 8/2007 | Friedlander | G16H 10/20 707/999.009 |
| 2007/0192140 A1* | 8/2007 | Gropper | G06F 21/6245 715/205 |
| 2007/0219824 A1* | 9/2007 | Rawlings | G06Q 10/10 705/2 |
| 2007/0294111 A1 | 12/2007 | Settimi | |
| 2008/0010254 A1* | 1/2008 | Settimi | G06Q 10/06 |
| 2008/0040151 A1* | 2/2008 | Moore | G16H 40/67 705/2 |
| 2008/0071577 A1* | 3/2008 | Highley | G06Q 10/10 705/50 |
| 2008/0097914 A1* | 4/2008 | Dicks | G16H 10/60 705/50 |
| 2008/0103554 A1* | 5/2008 | Dicks | G16H 40/67 607/60 |
| 2008/0120296 A1* | 5/2008 | Kariathungal | G16H 10/60 |
| 2008/0133273 A1* | 6/2008 | Marshall | G06Q 10/10 705/3 |
| 2008/0137848 A1* | 6/2008 | Kocher | H04L 9/302 380/201 |
| 2008/0147554 A1* | 6/2008 | Stevens | G16H 10/60 705/51 |
| 2008/0281631 A1* | 11/2008 | Syth | G16H 40/67 705/2 |
| 2008/0304663 A1* | 12/2008 | Canard | G06F 21/6254 380/45 |
| 2008/0306872 A1* | 12/2008 | Felsher | G06Q 10/10 705/51 |
| 2008/0306952 A1* | 12/2008 | Lynn | G16H 10/60 707/999.009 |

(56) References Cited

U.S. PATENT DOCUMENTS

| | | | |
|---|---|---|---|
| 2009/0024416 A1 | 1/2009 | McLaughlin et al. | |
| 2009/0070146 A1 | 3/2009 | Haider et al. | |
| 2009/0112769 A1 | 4/2009 | Dicks | |
| 2009/0171692 A1 | 7/2009 | Zilbeunan | |
| 2009/0257586 A1* | 10/2009 | Takahashi | G06K 9/00 358/448 |
| 2009/0287502 A1* | 11/2009 | Roberts | G06Q 40/08 705/3 |
| 2010/0034376 A1 | 2/2010 | Okuizumi et al. | |
| 2010/0114607 A1 | 5/2010 | Kress et al. | |
| 2010/0162355 A1* | 6/2010 | Zimmerman | G06Q 50/22 726/2 |
| 2010/0217973 A1* | 8/2010 | Kress | G06F 21/6254 713/153 |
| 2010/0287190 A1* | 11/2010 | Anderson | G16H 50/70 707/769 |
| 2010/0325148 A1* | 12/2010 | Anderson | G06F 16/3325 707/769 |
| 2011/0184748 A1* | 7/2011 | Fierro | G16H 40/67 705/2 |
| 2011/0191767 A1 | 8/2011 | Pinsky | |
| 2011/0191822 A1 | 8/2011 | Pinsky | |
| 2011/0196704 A1 | 8/2011 | Mansour | |
| 2011/0225007 A1 | 9/2011 | Theis | |
| 2011/0231422 A1* | 9/2011 | Rawlings | G16H 50/70 707/E17.014 |
| 2011/0255690 A1* | 10/2011 | Kocher | H04L 9/3236 380/210 |
| 2011/0258000 A1 | 10/2011 | Green et al. | |
| 2012/0246661 A1* | 9/2012 | Nishimura | G06F 40/00 718/106 |
| 2013/0246334 A1 | 9/2013 | Ahuja | |
| 2014/0053252 A1 | 2/2014 | Kelsey | |
| 2014/0108038 A1* | 4/2014 | Lipsky | G06Q 30/04 705/2 |
| 2015/0046192 A1 | 2/2015 | Raduchel | |
| 2016/0314248 A1* | 10/2016 | Klocek | G16H 10/60 |
| 2017/0316530 A1 | 11/2017 | Kress et al. | |

FOREIGN PATENT DOCUMENTS

| | | |
|---|---|---|
| WO | WO 2004/031922 | 4/2004 |
| WO | WO 2007/108814 | 9/2007 |
| WO | WO 2010/129653 | 11/2010 |

OTHER PUBLICATIONS

"Health Information Privacy: Business Associates," U.S. Department of Health and Human Services, Apr. 3, 2003, Retrieved online: http://www.hhs.gov/ocr/privacy/hipaa/understanding/coveredentities/businessassociates.html, (accessed Oct. 9, 2014), 2 pages.

Claerhout et al., "Privacy protection for clinical and genomic data. The use of privacy-enhancing techniques in medicine, "Int. J. Med. Informatics, Mar. 2005, 74:257-265.

Eman et al., "Protecting Privacy Using k-Anonymity," J Am Med Inform Assoc., Sep. 2008, 15:627-637.

Federal Register, "Department of Health and Human Services, 45 CFR Parts 160 and 164 Standards for Privacy of Individually Identifiable Health Information; Final Rule," National Archives and Records Administration, Dec. 28, 2000, 419 pages.

Group Insurance, 5th ed., ACTEX Publications, Jan. 2007, Chapter 28: Health Risk Adjustment, 29 pages.

Malin et al., "An Evaluation of the Current State of Genomic Data Privacy Protection Technology and a Roadmap for the Future," J. Am. Med. Inform. Assoc., Jan. 2005, 12:28-34.

Milliman, Inc., et al. Plaintiff v. Gradient A.I. Corp., et al., Defendant, United States District Court for the District of Massachusetts, Civil Action No. 1:21-CV-10865-NMG, Summons in a Civil Action, filed May 25, 2021, 2 pages (case 1:21-cv-10865-NMG, D6).

Milliman, Inc., et al. Plaintiff v. Gradient A.I. Corp., et al., Defendant, United States District Court for the District of Massachusetts, Civil Action No. 1:21-CV-10865-NMG, Summons in a Civil Action, filed May 26, 2021, 2 pages (case 1:21-cv-10865-NMG, D9).

Milliman, Inc., et al., Plaintiffs, v. Gradient A.I. Corp., et al., Defendants. Memorandum & Order, filed on Jan. 19, 2023, 13 pages (Civil Action No. 21-10865-NMG, D133).

Milliman, Inc., et al., Plaintiffs, v. Gradient A.I. Corp., et al., Defendants. Memorandum & Order, filed on Jan. 19, 2023, 17 pages (Civil Action No. 21-10865-NMG, D134).

Milliman, Inc., et al., Plaintiffs, v. Gradient A.I. Corp., et al., Defendants. United States District Court District of Massachusetts, Memorandum and Order on Motion to Compel and Cross Motion for Protective Order (##54, 59), filed Jul. 11, 2022, 6 pages (case 1:21-cv-10865-NMG, D70).

Milliman, Inc., et al., Plaintiffs, v. Gradient A.I. Corp., et al., Defendants. United States District Court District of Massachusetts, Order, Filed on Apr. 7, 2022, 3 pages (case 1:21-cv-10865-NMG, D52).

Milliman, Inc., Milliman Solutions, LLC, and Vigilytics LLC, Plaintiffs, vs. Gradient A.I. Corp., Stanford A. Smith, and Samuel Chase Pettus, Defendants. Affidavit of Kevin C. Quigley in Support of Defendant Gradient'S Responsive Claim Construction Brief, filed on Dec. 8, 2022, 3 pages (case 1:21-cv-10865-NMG, D129).

Milliman, Inc., Milliman Solutions, LLC, and Vigilytics LLC, Plaintiffs, vs. Gradient A.I. Corp., Stanford A. Smith, and Samuel Chase Pettus, Defendants. Declaration of Mark G. Knedeisen in Support of Plaintiffs' Responsive Claim Construction Brief, Exhibit A, filed on Dec. 8, 2022, 216 pages (Case 1:21-cv-10865-NMG, D127-1).

Milliman, Inc., Milliman Solutions, LLC, and Vigilytics LLC, Plaintiffs, vs. Gradient A.I. Corp., Stanford A. Smith, and Samuel Chase Pettus, Defendants. Declaration of Mark G. Knedeisen in Support of Plaintiffs' Responsive Claim Construction Brief, filed on Dec. 8, 2022, 1 page (Case 1:21-cv-10865, D127).

Milliman, Inc., Milliman Solutions, LLC, and Vigilytics LLC, Plaintiffs, vs. Gradient A.I. Corp., Stanford A. Smith, and Samuel Chase Pettus, Defendants. Defendant Gradient'S Responsive Claim Construction Brief, filed on Dec. 8, 2022, 24 pages (case 1:21-cv-10865-NMG, D128).

Milliman, Inc., Milliman Solutions, LLC, and Vigilytics LLCPlaintiffs, vs. Gradient A.I. Corp., Stanford A. Smith, and Samuel Chase Pettus, Defendants. Defendants' Preliminary Invalidity Contentions, dated Aug. 25, 2022, 65 pages (case 1:21-cv-10865-NMG).

Milliman, Inc., Milliman Solutions, LLC, and Vigilytics LLC, Plaintiffs, vs. Gradient A.I. Corp., Stanford A. Smith, and Samuel Chase Pettus, Defendants. Defendants' Preliminary Invalidity Contentions, Exhibit 1-A: Preliminary Invalidity Contentions for U.S. Pat. No. 9,118,641 dated Aug. 25, 2022, 30 pages (case 1:21-cv-10865-NMG, 1-A).

Milliman, Inc., Milliman Solutions, LLC, and Vigilytics LLC, Plaintiffs, vs. Gradient A.I. Corp., Stanford A. Smith, and Samuel Chase Pettus, Defendants. Defendants' Preliminary Invalidity Contentions, Exhibit 1-B: Preliminary Invalidity Contentions for U.S. Pat. No. 9,118,641, dated Aug. 25, 2022, 38 pages (case 1:21-cv-10865-NMG, 1-B).

Milliman, Inc., Milliman Solutions, LLC, and Vigilytics LLC, Plaintiffs, vs. Gradient A.I. Corp., Stanford A. Smith, and Samuel Chase Pettus, Defendants. Defendants' Preliminary Invalidity Contentions, Exhibit 1-C: Preliminary Invalidity Contentions for U.S. Pat. No. 9,118,641, dated Aug. 25, 2022, 43 pages (case 1:21-cv-10865-NMG, 1-C).

Milliman, Inc., Milliman Solutions, LLC, and Vigilytics LLC, Plaintiffs, vs. Gradient A.I. Corp., Stanford A. Smith, and Samuel Chase Pettus, Defendants. Defendants' Preliminary Invalidity Contentions, Exhibit 1-D: Preliminary Invalidity Contentions for U.S. Pat. No. 9,118,641, dated Aug. 25, 2022, 42 pages (Case 1:21-cv-10865-NMG, 1-D).

Milliman, Inc., Milliman Solutions, LLC, and Vigilytics LLC, Plaintiffs, vs. Gradient A.I. Corp., Stanford A. Smith, and Samuel Chase Pettus, Defendants. Defendants' Preliminary Invalidity Contentions, Exhibit 2-A: Preliminary Invalidity Contentions for U.S. Pat. No. 10,109,375, dated Aug. 25, 2022, 21 pages (Case 1:21-cv-10865-NMG, 2-A).

Milliman, Inc., Milliman Solutions, LLC, and Vigilytics LLC, Plaintiffs, vs. Gradient A.I. Corp., Stanford A. Smith, and Samuel Chase

(56) References Cited

OTHER PUBLICATIONS

*Pettus*, Defendants. Defendants' Preliminary Invalidity Contentions, Exhibit 2-B: Preliminary Invalidity Contentions for U.S. Pat. No. 10,109,375, dated Aug. 25, 2022, 27 pages (Case 1:21-cv-10865-NMG, 2-B).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Invalidity Contentions, Exhibit 2-C: Preliminary Invalidity Contentions for U.S. Pat. No. 10,109,375, dated Aug. 25, 2022, 31 pages (Case 1:21-cv-10865-NMG, 2-C).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Invalidity Contentions, Exhibit 2-D: Preliminary Invalidity Contentions for U.S. Pat. No. 10,109,375, dated Aug. 25, 2022, 30 pages (Case 1:21-cv-10865-NMG, 2-D).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Invalidity Contentions, Exhibit 3-A: Preliminary Invalidity Contentions for U.S. Pat. No. 10,886,012, dated Aug. 25, 2022, 17 pages (Case 1:21-cv-10865-NMG, 3-A).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Invalidity Contentions, Exhibit 3-B: Preliminary Invalidity Contentions for U.S. Pat. No. 10,886,012. dated Aug. 25, 2022, 22 pages (Case 1:21-cv-10865-NMG, 3-B).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Invalidity Contentions, Exhibit 3-C: Preliminary Invalidity Contentions for U.S. Pat. No. 10,886,012, dated Aug. 25, 2022, 26 pages (Case 1:21-cv-10865-NMG, 3-C).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Invalidity Contentions, Exhibit 3-D: Preliminary Invalidity Contentions for U.S. Pat. No. 10,886,012, dated Aug. 25, 2022, 25 pages (Case 1:21-cv-10865-NMG, 3-D).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Invalidity Contentions, Exhibit 4-A: Preliminary Invalidity Contentions for U.S. Pat. No. 9,323,892, dated Aug. 25, 2022, 17 pages (Case 1:21-cv-10865-NMG, 4-A).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Invalidity Contentions, Exhibit 4-B: Preliminary Invalidity Contentions for U.S. Pat. No. 9,323,892, dated Aug. 25, 2022, 19 pages (Case 1:21-cv-10865-NMG, 4-B).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Invalidity Contentions, Exhibit 4-C: Preliminary Invalidity Contentions for U.S. Pat. No. 9,323,892, dated Aug. 25, 2022, 23 pages (Case 1:21-cv-10865-NMG, 4-C).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Invalidity Contentions, Exhibit 4-D: Preliminary Invalidity Contentions for U.S. Pat. No. 9,323,892, dated Aug. 25, 2022, 14 pages (Case 1:21-cv-10865-NMG, 4-D).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Invalidity Contentions, Exhibit 5-A: Preliminary Invalidity Contentions for U.S. Pat. No. 9,665,685, dated Aug. 25, 2022, 25 pages (Case 1:21-cv-10865-NMG, 5-A).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Invalidity Contentions, Exhibit 5-B: Preliminary Invalidity Contentions for U.S. Pat. No. 9,665,685, dated Aug. 25, 2022, 38 pages (Case 1:21-cv-10865-NMG, 5-B).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Invalidity Contentions, Exhibit 5-C: Preliminary Invalidity Contentions for U.S. Pat. No. 9,665,685, dated Aug. 25, 2022, 42 pages (Case 1:21-cv-10865-NMG, 5-C).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Invalidity Contentions, Exhibit 5-D: Preliminary Invalidity Contentions for U.S. Pat. No. 9,665,685, dated Aug. 25, 2022, 42 pages (Case 1:21-cv-10865-NMG, 5-D).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Invalidity Contentions, Exhibit 6-A: Preliminary Invalidity Contentions for U.S. Pat. No. 9,965,651, dated Aug. 25, 2022, 30 pages (Case 1:21-cv-10865-NMG, 6-A).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Invalidity Contentions, Exhibit 6-B: Preliminary Invalidity Contentions for U.S. Pat. No. 9,965,651, dated Aug. 25, 2022, 42 pages (Case 1:21-cv-10865-NMG, 6-B).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Invalidity Contentions, Exhibit 6-C: Preliminary Invalidity Contentions for U.S. Pat. No. 9,965,651, dated Aug. 25, 2022, 46 pages (Case 1:21-cv-10865-NMG, 6-C).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Invalidity Contentions, Exhibit 6-D: Preliminary Invalidity Contentions for U.S. Pat. No. 9,965,651, dated Aug. 22, 2022, 46 pages (Case 1:21-cv-10865-NMG, 6-D).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Non-Infringement Contentions, Exhibit 1: Preliminary Non-Infringement Contentions for U.S. Pat. No. 9,118,641, dated Aug. 25, 2022, 2 pages (Case 1:21-cv-10865-NMG, Exhibit 1).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Non-Infringement Contentions, Exhibit 2: Preliminary Non-Infringement Contentions for U.S. Pat. No. 10,109,375, dated Aug. 25, 2022, 2 pages (Case 1:21-cv-10865-NMG, Exhibit 2).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Non-Infringement Contentions, Exhibit 3: Preliminary Non-Infringement Contentions for U.S. Pat. No. 10,886,012, dated Aug. 25, 2022, 1 page (Case 1:21-cv-10865-NMG, Exhibit 3).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Non-Infringement Contentions, Exhibit 4: Preliminary Non-Infringement Contentions for U.S. Pat. No. 9,323,892, dated Aug. 25, 2022, 2 pages (Case 1:21-cv-10865-NMG, Exhibit 4).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Non-Infringement Contentions, Exhibit 5: Preliminary Non-Infringement Contentions for

(56) References Cited

OTHER PUBLICATIONS

U.S. Pat. No. 9,665,685, dated Aug. 25, 2022, 2 pages (Case 1:21-cv-10865-NMG, Exhibit 5).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Noninfringement Contentions, Exhibit 6: Preliminary Noninfringement Contentions for U.S. Pat. No. 9,965,651, dated Aug. 25, 2022, 2 pages (Case 1:21-cv-10865-NMG, Exhibit 6).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Noninfringement Contentions, filed on Aug. 25, 2022, 6 pages (Case 1:21-cv-10865-NMG).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. Exhibit 5, Deposition of Aviel D. Rubin, Ph D., filed on Dec. 8, 2022, 86 pages (case 1:21-cv-10865-NMG, 129-1).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. Exhibit 6, Plaintiffs' Disclosure of Claim Terms and Proposed Preliminary Constructions, filed on Dec. 8, 2022, 6 pages (case 1:21-cv-10865-NMG, 129-2).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. Exhibit 7, Defendants' List of Claim Terms To Be Construed and Their Proposed Constructions, filed on Dec. 8, 2022, 8 pages (case 1:21-cv-10865-NMG, D129-3).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Ex A to Pltfs Opp to Defs Partial Mot to Dismiss for Failure to State a Claim, filed Jul. 26, 2021, 17 pages (case 21-cv-10865, D26-2).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Ex B to Pltfs Opp to Defs Partial Mot to Dismiss for Failure to State a Claim, filed Jul. 26, 2021, 2 pages (Case 21-cv-10865, D26-3).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, [Proposed] Order Establishing Protocol Governing Production of Documents and Electronically Stored Information ("ESI"), Exhibit B, filed on Mar. 25, 2022, 15 pages (Case 1:21-cv-10865-NMG, D48-2).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, [Proposed] Order On Defendants' Cross-Motion for a Protective Order, filed on May 25, 2022, 1 page (case 1:21-cv-10865-NMG, D59-1).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, [Proposed] Plaintiffs' Surreply in Opposition To Defendants' Partial Motion to Dismiss for Failure to State A Claim Exhibit A, filed Aug. 11, 2021, 12 pages (case Civil Action No. 21-cv-10865, D30-1).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, [Proposed] Protective Order, Exhibit A, filed on Mar. 25, 2022, 34 pages (Case 1:21-cv-10865-NMG, D48-1).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, [Proposed] Scheduling Order, Exhibit A, filed on Mar. 28, 2022, 6 pages (Case 1:21-cv-10865-NMG, D50-1).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, [Proposed] Scheduling Order, filed Mar. 14, 2022, 5 pages, (case 1:21-cv-10865-NMG, D44).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Affidavit of Kevin C. Quigley in Support of Defendants' Motion for Summary Judgment, filed Sep. 16, 2022, 2 pages (Case 1:21-cv-10865-NMG, D91).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Affidavit of Kevin C. Quigley in Support of Defendants' Motion for Summary Judgment, filed on Oct. 20, 2022, 2 pages (Case 1:21-cv-10865-NMG, Dill).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Answer and Counterclaims of Defendants Gradient A.I. Corp., Stanford A. Smith, and Samuel Chase Pettus, filed on Mar. 25, 2022, 64 pages (case 1:21-cv-10865-NMG).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Assented-to Motion for Leave to File Reply in Support of Plaintiffs' Motion To Compel Compliance With the Court'S Automatic Patent Disclosures, filed on Oct. 21, 2022, 4 pages (Case 1:21-cv-10865-NMG, D113).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Asset Purchase Agreement, Exhibit A, filed Mar. 25, 2022, 27 pages (Case 1:21-cv-10865-NMG, D49-1).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Certification of Milliman, Inc., Milliman Solutions, LLC, and Vigilytics, LLC Pursuant to Local Rule 16.1, filed on Mar. 3, 2022, 3 pages (case 1:21-cv-10865, D42).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Combined Statement of Facts Regardingdefendants' Motion for Summary Judgment On Milliman'S Trade Secret Claims, filed on Oct. 28, 2022, 31 pages (Case 1:21-cv-10865-NMG, D119).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Dr. Aviel D. Rubin, Exhibit A, filed Sep. 16, 2022, 47 pages (case 1:21-cv-10865-NMG, D86-1).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Kevin C. Quigley, Exhibit 1, Filed on Oct. 20, 2022, 14 pages (Case 1:21-cv-10865-NMG, D111-1).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Kevin C. Quigley, Exhibit 2, filed on Oct. 20, 2022, 12 pages (Case 1:21-cv-10865-NMG, D111-2).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the

(56) References Cited

OTHER PUBLICATIONS

District of Massachusetts, Declaration of Kevin C. Quigley, Exhibit 3, filed on Oct. 20, 2022, 76 pages (Case 1:21-cv-10865-NMG, D111-3).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Kevin C. Quigley, Exhibit 4, filed on Oct. 20, 2022, 9 pages (Case 1:21-cv-10865-NMG, D111-4).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Mark G. Knedeisen in Support of Plaintiffs' Opening Claim Construction Brief, Exhibit 3, filed on Oct. 20, 2022, 20 pages (Case 1:21-cv-10865-NMG, D109-3).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Mark G. Knedeisen in Support of Plaintiffs' Opening Claim Construction Brief, Exhibit 4, filed on Oct. 20, 2022, 11 pages (Case 1:21-cv-10865-NMG, D109-4).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Mark G. Knedeisen in Support of Plaintiffs' Opening Claim Construction Brief, Exhibit 5, filed on Oct. 20, 2022, 15 pages (Case 1:21-cv-10865-NMG, D109-5).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Mark G. Knedeisen in Support of Plaintiffs' Opening Claim Construction Brief, Exhibit 6, filed on Oct. 20, 2022, 6 pages (Case 1:21-cv-10865-NMG, D109-6).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Mark G. Knedeisen in Support of Plaintiffs' Opening Claim Construction Brief, Exhibit 7, filed on Oct. 20, 2022, 8 pages (Case 1:21-cv-10865-NMG, D109-7).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Mark G. Knedeisen in Support of Plaintiffs' Opening Claim Construction Brief, Exhibit 8, filed on Oct. 20, 2022, 6 pages (Case 1:21-cv-10865-NMG, D109-8).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Mark G. Knedeisen in Support of Plaintiffs' Opening Claim Construction Brief, Exhibit 9, filed on Oct. 20, 2022, 6 pages (Case 1:21-cv-10865-NMG, D109-9).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Mark G. Knedeisen in Support of Plaintiffs' Opening Claim Construction Brief, Exhibit 10, filed on Oct. 20, 2022, 6 pages (Case 1:21-cv-10865-NMG, D109-10).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Mark G. Knedeisen in Support of Plaintiffs' Opening Claim Construction Brief, Exhibit 11, filed on Oct. 20, 2022, 6 pages (Case 1:21-cv-10865-NMG, D109-11).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Mark G. Knedeisen in Support of Plaintiffs' Opening Claim Construction Brief, filed on Oct. 20, 2022, 3 pages (Case 1:21-cv-10865-NMG, D109).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Mark G. Knedeisen in Support of Plaintiffs' Opening Claim Construction Brief, Declaration of Dr. Aviel D. Rubin, Exhibit 1, filed on Oct. 20, 2022, 49 pages (Case 1:21-cv-10865-NMG, D 109-1).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Mark G. Knedeisen in Support of Plaintiffs' Opening Claim Construction Brief, Exhibit 2, filed on Oct. 20, 2022, 15 pages (Case 1:21-cv-10865-NMG, D109-2).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Noah C. Graubart in Support of Plaintiffs' Opposition to Defendants' Partial Motion to Dismiss for Failure to State a Claim, filed Jul. 26, 2021, 2 pages (case 21-cv-10865, D26-1).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Sophie F. Wang, Esq. in Support of Memorandum in Support of Defendants' Partial Motion to Dismiss for Failure to State a Claim, filed Jul. 7, 2021, 27 pages, (case 1:21-cv-10865-NMG, D23).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Stephen A. White, filed Oct. 14, 2022, 10 pages (Case 1:21-cv-10865-NMG, D106).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Stephen A. White, Exhibit A, filed Oct. 14, 2022, 27 pages (Case 1:21-cv-10865-NMG, D106-1).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Stephen A. White, Exhibit B, filed Oct. 14, 2022, 10 pages (case 1:21-cv-10865-NMG, D106-2).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Stephen A. White, Exhibit C, filed Oct. 14, 2022, 2 pages (Case 1:21-cv-10865-NMG, D106-3).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Stephen A. White, Exhibit D, Filed on Oct. 14, 2022, 2 pages (Case 1:21-cv-10865-NMG, D106-4).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Stephen A. White, Exhibit E, filed on Oct. 14, 2022, 2 pages (Case 1:21-cv-10865-NMG, D106-5).

(56) References Cited

OTHER PUBLICATIONS

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Stephen A. White, Exhibit F, filed on Oct. 14, 2022, 2 pages (Case 1:21-cv-10865-NMG, D106-6).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Stephen A. White, Exhibit G, filed on Oct. 14, 2022, 2 pages (Case 1:21-cv-10865-NMG, D106-7).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Stephen A. White, Exhibit H, filed on Oct. 14, 2022, 2 pages (Case 1:21-cv-10865-NMG, D106-8).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Stephen A. White, Exhibit I, filed on Oct. 14, 2022, 2 page (Case 1:21-cv-10865-NMG, D106-9).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Stephen A. White, Exhibit J, filed on Oct. 14, 2022, 2 pages (Case 1:21-cv-10865-NMG, D106-10).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Stephen A. White, Exhibit K, filed on Oct. 14, 2022, 2 pages (Case 1:21-cv-10865-NMG, D106-11).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Stephen A. White, Exhibit L, filed on Oct. 14, 2022, 2 pages (Case 1:21-cv-10865-NMG, D106-12).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Stephen A. White, Exhibit M, filed on Oct. 1, 2022, 2 pages (Case 1:21-cv-10865-NMG, D106-13).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Defendant Gradient A.I. Corp.'S Corporate Disclosure Statement, filed Jul. 7, 2021, 2 pages (case 1:21-cv-10865-NMG, D20).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Defendant Gradient'S Opening Claim Construction Brief, filed on Oct. 20, 2022, 24 pages (Case 1:21-cv-10865-NMG, D110).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Defendants' Motion for Extension of Time to Answer or Respond to Complaint, filed Jun. 16, 2021, 1 page (case 1:21-cv-10865-NMG, DI5).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Defendants' Assented-to Motion for Leave to File a Reply Brief in Support of Defendants' Partial Motion to Dismiss for Failure to State a Claim, filed Aug. 3, 2021, 3 pages (Civil Action No. 1:21-cv-10865-NMG, D27).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Defendants' Assented-to Motion for Leave to File Under Seal, filed on Aug. 25, 2022, (case 1:21-cv-10865-NMG, D76).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Defendants' Assented-to Motion for Leave to File Under Seal, filed on Sep. 16, 2022, 2 pages (Case 1:21-cv-10865-NMG, D92).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Defendants' Assented-to Motion for Leave to File Under Seal, Filed Sep. 30, 2022, 2 pages (Case 1:21-cv-10865-NMG, D100).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Defendants' Cross-Motion for a Protective Order, filed on May 25, 2022, 3 pages (Case 1:21-cv-10865-NMG, D59).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Defendants' Local Rule 16.1(D)(3) Certification, filed on Mar. 3, 2022, 2 pages (Case 1:21-cv-10865-NMG, D40).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Defendants' Memorandum in Support of Summary Judgment On Milliman'S Trade Secret Claims, filed Sep. 16, 2022, 21 pages, (case 1:21-cv-10865-NMG, D89).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Defendants' Motion for Extension of Time to Answer or Respond to Complaint, filed Jun. 16, 2021, 7 pages (case 1:21-cv-10865-NMG, D13).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Defendants' Motion for Summary Judgment On Milliman'S Trade Secret Claims (Counts VII-XII), filed on Sep. 16, 2022, 2 pages (case 1:21-cv-10865-NMG, D88).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Defendants' Partial Motion to Dismiss for Failure to State a Claim, filed Jul. 7, 2021, 2 pages (1:21-cv-10865-NMG, D21).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Defendants' Preliminary Non-Infringement Contentions, Exhibit H, filed Sep. 16, 2022, 18 pages (Case 1:21-cv-10865-NMG, D86-8).
*Milliman, Inc., Milliman Solutions, LLC, and Vigilytics LLC*, Plaintiffs, vs. Gradient A.I. Corp., Stanford A. Smith, and Samuel Chase Pettus, Defendants. In the United States District Court for the District of Massachusetts, Defendants' Reply in Support of Summary Judgment, filed on Oct. 28, 2022, 9 pages (Case 1:21-cv-10865-NMG, D118).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the

(56) References Cited

OTHER PUBLICATIONS

District of Massachusetts, Defendants' Request for Leave to File Summary Judgment Reply, filed on Oct. 20, 2022, 2 pages (Case 1:21-cv-10865-NMG, D107).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Defendants' Responses and Objections to Plaintiffs' First Set of Interrogatories to Defendants, Exhibit D, filed on May 11, 2022, 21 pages (Case 1:21-cv-10865-NMG, D55-4).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Defendants' Responses and Objections to Plaintiffs' First Set of Requests for Production of Documents and Things to Defendants, Exhibit E, filed on May 11, 2022, 50 pages (Case 1:21-cv-10865-NMG, D55-5).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Defendants' Statement of Undisputed Material Facts Supporting Summary Judgment on Milliman'S Trade Secret Claims, filed Sep. 16, 2022, 8 pages (case 1:21-cv-10865-NMG, D90).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Exhibit A, United States Court of Appeals for the Federal Circuit, PersonalWeb Technologies LLC, Plaintiff-Appellant, Google LLC, Youtube, LLC, Defendants-Appellees, 2020-1553, filed Aug. 24, 2021, 17 pages (case Civil Action No. 1:21-cv-10865-NMG, D33-1).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Exhibit B, filed Mar. 25, 2022, 7 pages (case 1:21-cv-10865-NMG, D49-2).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Exhibit F, filed on May 11, 2022, 6 pages (case 1:21-cv-10865-NMG, D55-6).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Gradient'S Memorandum (1) In Opposition to Milliman'S Motion to Compel; and (2) In Support of Cross-Motion for Protective Order, filed on May 25, 2022, 19 pages (case 1:21-cv-10865-NMG, D60).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Gradient'S Opposition to Milliman'S Renewed Motion to Compel, Redacted , filed Aug. 26, 2022, 9 pages (case 1:21-cv-10865-NMG, D78).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Gradient'S Opposition To Plaintiffs' L.R. 16.6 Motion to Compel, filed on Sep. 30, 2022, 8 pages (Case 1:21-cv-10865-NMG, D99).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Gradient'S Supplemental Memorandum Regarding Trade Secret Identification, filed Jun. 23, 2022, 6 pages (case 1:21-cv-10865-NMG, D64).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Joint Claim Construction Statement, filed on Sep. 29, 2022, 11 pages (Case 1:21-cv-10865-NMG, D98).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Joint Motion for Entry of [Proposed] Scheduling Order, filed Mar. 28, 2022, 3 pages (Case 1:21-cv-10865-NMG, D50).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Joint Motion for Entry of Protective Order and Order Establishing Protocol Governing Production of Documents and Electronically Stored Information, filed on Mar. 25, 2022, 4 pages (case Civil Action No. 1:21-cv-10865-NMG, D48).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Joint Motion for Entry of Protective Order and Order Establishing Protocol Governing Production of Documents and Electronically Stored Information, filed on Apr. 6, 2022, 1 page (Case 1:21-cv-10865-NMG, D51).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Joint Statement, Filed on Mar. 3, 2022, 16 pages (case 1:21-cv-10865-NMG, D41).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Memorandum and Order on Motions to Compel (##71, 85), filed on Nov. 10, 2022, 8 pages (Case 1:21-cv-10865-NMG, D123).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Memorandum in Support of Defendants' Partial Motion To Dismiss for Failure to State a Claim, filed Jul. 7, 2021, 25 pages (case 1:21-cv-10865-NMG, D22).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Memorandum in Support of Plaintiffs' Motion To Compel Discovery Responses, filed on May 11, 2022, 16 pages (case 1:21-cv-10865-NMG, D55).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Memorandum in Support of Plaintiffs' Renewed Motion To Compel Discovery Responses, filed on Aug. 12, 2022, 12 pages (case 1:21-cv-10865-NMG, D72).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Memorandum in Support of Plaintiffs' Renewed Motion to Compel Discovery Responses, Exhibit E, filed on Aug. 12, 2022, (case 1:21-cv-10865-NMG, D72-5).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Motion for Admission Pro Hac Vice of Patrick J. McElhinny, Mark G. Knedeisen and Anna Shabalov, filed on May 26, 2021, 8 pages (case 1:21-cv-10865-NMG, D8).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Motion for Admission Pro Hac Vice of Noah C. Graubart and Joseph R. Dorris, filed on Jun. 1, 2021, 2 pages (case 1:21-cv-10865-NMG, D11).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the

(56) References Cited

OTHER PUBLICATIONS

District of Massachusetts, Notice of Appearance, filed Jul. 7, 2021, 1 page (case 1:21-cv-10865-NMG, D17).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Notice of Appearance, filed Jul. 7, 2021, 1 page (case 1:21-cv-10865-NMG, D18).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Notice of Appearance, filed Jul. 7, 2021, 1 page (case 1:21-cv-10865-NMG, D19).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Notice of Appearance, filed Mar. 14, 2022, 1 page, (case 1:21-cv-10865-NMG, D45).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Notice of Appearance, filed on Mar. 25, 2022, 1 page (case Civil Action No. 1:21-cv-10865-NMG, D47).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Notice of Appearance, filed on Nov. 10, 2022, 2 pages (Case 1:21-cv-10865-NMG, D122).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Notice of Supplemental Authority in Support of Defendants' Partial Motion to Dismiss, filed Aug. 24, 2021, 3 pages (case Civil Action No. 1:21-cv-10865-NMG, D33).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Notice Regarding Timing of Defendants' Forthcoming Motion for Partial Summary Judgment, filed on Sep. 7, 2022, 1 page (Case 1:21-cv-10865-NMG, D84).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Plaintiffs' Answer to Defendants' Counterclaims, filed Apr. 15, 2022, 21 pages (case 1:21-cv-10865-NMG, D53).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Plaintiffs' Assented-to Motion for Leave to File a Surreply Brief in Opposition To Defendants' Partial Motion to Dismiss for Failure to State a Claim, filed on Aug. 11, 2021, 3 pages (Case Civil Action No. 21-cv-10865, D30).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Plaintiffs' First Set of Interrogatories to Defendants, Exhibit B, filed on May 11, 2022, 10 pages (case 1:21-cv-10865-NMG, D55-2).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Plaintiffs' First Set of Requests for Production of Documents and Things to Defendants, Exhibit C, filed on May 11, 2022, 17 pages (Case 1:21-cv-10865-NMG, D55-3).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Plaintiffs' Memorandum in Opposition to Defendants' Motion for Summary Judgment on Milliman'S Trade Secret Claims, filed on Oct. 14, 2022, 26 pages (case 1:21-cv-10865-NMG, D104).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Plaintiffs' Memorandum in Support of Their Motion to Compel Compliance With the Court'S Automatic Patent Disclosures, filed on Sep. 16, 2022, 24 pages (Case 1:21-cv-10865-NMG, D86).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Plaintiffs' Motion to Compel Compliance With Automatic Patent Disclosures, filed Sep. 16, 2022, 4 pages (Case 1:21-cv-10865-NMG, D85).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Plaintiffs' Motion to Compel Discovery Responses, filed May 11, 2022, 4 pages (case 1:21-cv-10865-NMG, D54).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Plaintiffs' Opening Claim Construction Brief, filed on Oct. 20, 2022, 28 pages (Case 1:21-cv-10865-NMG, D108).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Plaintiffs' Opposition To Defendants' Motion for a Sixty ("60") Day Extension of Time to Answer or Respond to Complaint, Filed Jun. 16, 2021, 13 pages (case 1:21-cv-10865, D14).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Plaintiffs' Opposition to Defendants' Partial Motion to Dismiss for Failure to State a Claim, filed Jul. 26, 2021, 27 pages, (case 21-cv-10865, D26).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Plaintiffs' Opposition to Defendants' Motion for Protective Order, filed on Jun. 8, 2022, 16 pages (Case 1:21-cv-10865-NMG, D62).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Plaintiffs' Renewed Motion to Compel Discovery Responses, filed on Aug. 12, 2022, 4 pages (case 1:21-cv-10865-NMG, D71).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Plaintiffs' Reply in Support of Their Motion to Compel Compliance With the Court'S Automatic Patent Disclosures, filed on Oct. 21, 2022, 13 pages (Case 1:21-cv-10865-NMG, D113-1).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Plaintiffs' Reply in Support of Their Motion to Compel Compliance With the Court'S Automatic Patent Disclosures, filed on Oct. 24, 2022, 13 pages (Case 1:21-cv-10865-NMG, D115).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Plaintiffs' Response to Defendants' Notice of Supplemental Authority, filed Sep. 1, 2021, 5 pages (case Civil Action No. 21-cv-10865, D34-1).

(56) References Cited

OTHER PUBLICATIONS

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Plaintiffs' Response To Defendants' Notice of Supplemental Authority, filed Sep. 2, 2021, 5 pages (Case Civil Action No. 21-cv-10865, D36).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Plaintiffs' Response to Defendants' Statement of Allegedly Undisputed Material Facts Supporting Summary Judgment on Milliman'S Trade Secret Claims, filed on Oct. 14, 2022, 28 pages (Case 1:21-cv-10865-NMG, D105).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Plaintiffs' Supplemental Brief Regarding Applicability of the Massachusetts Uniform Trade Secrets Act, filed on Jun. 23, 2022, 11 pages (Case 1:21-cv-10865-NMG, D65).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Plaintiffs' Surreply in Opposition to Defendants' Partial Motion to Dismiss for Failure to State a Claim, filed Aug. 12, 2021, 11 pages (Case Civil Action No. 21-cv-10865, D32).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Plaintiffs' Unopposed Motion for Extension of Time to Respond to Defendants' Motion to Dismiss, filed Jul. 15, 2021, 5 pages, (case 21-cv-10865-NMG, D24).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Plaintiffs' Unopposed Motion for Leave to File Response to Defendants' Notice of Supplemental Authority in Support of Their Partial Motion to Dismiss, filed Sep. 1, 2021, 4 pages, (Case 21-cv-10865, D34).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Plaintiffs' Unopposed Motion for an Order Setting a Scheduling Conference, filed on Feb. 7, 2022, 3 pages (Case Civil Action No. 21-cv-10865, D37).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Plaintiffs' Unopposed Motion for Leave to File Under Seal, filed on May 11, 2022, 4 pages (Case 1:21-cv-10865-NMG, D56).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Plaintiffs' Unopposed Motion for Leave to File Under Seal, filed Aug. 12, 2022, (case 1:21-cv-10865-NMG, D73).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Plaintiffs' Unopposed Motion for Leave to File Reply in Support of Motion to Compel, filed on Sep. 2, 2022, 4 pages (Case 1:21-cv-10865-NMG, D79).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Plaintiffs' Unopposed Motion for Leave to File Reply in Support of Motion to Compel, Exhibit A, filed on Sep. 2, 2022, 5 pages (case 1:21-cv-10865-NMG, D79-2).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Plaintiffs' Unopposed Motion for Leave to File Under Seal, filed Sep. 16, 2022, 4 pages (Case 1:21-cv-10865-NMG, D87).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Plaintiffs' Unopposed Supplemental Motion for Leave to File Under Seal, filed on Jul. 7, 2022, 4 pages (Case 1:21-cv-10865-NMG, D67).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Reply Brief in Support of Defendants' Partial Motion to Dismiss for Failure to State a Claim, filed on Aug. 4, 2021, 13 pages (case 1:21-cv-10865-NMG, D29).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Reply in Support of Plaintiffs' Renewed Motion to Compel Discovery Responses, filed on Sep. 2, 2022, 11 pages (Case 1:21-cv-10865-NMG, D79-1).
*Milliman, Inc., Milliman Solutions, LLC and Vigilytics LLC*, Plaintiffs, vs. *Gradient A.I. Corp., Stanford A. Smith, and Samuel Chase Pettus*, Defendants. In the United States District Court for the District of Massachusetts, Reply in Support of Plain Fifes' Renewed Motion to Compel Discovery Responses, filed on Sep. 6, 2022, 16 pages (Case 1:21-cv-10865-NMG, D83).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Rule 7.1 Corporate Disclosure Statement, filed on May 26, 2021, 2 pages (case 1:21-cv-10865-NMG, D7).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Rule 7.1 Corporate Disclosure Statement, filed on May 25, 2021, 2 pages (case 1:21-cv-10865-NMG, D3).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Rule 7.1 Corporate Disclosure Statement, filed on May 25, 2021, 2 pages (case 1:21-cv-10865-NMG, D4).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts,[Proposed] Reply Brief in Support of Defendants' Partial Motion to Dismiss for Failure to State a Claim, Exhibit A, filed on Aug. 3, 2021, 14 pages (Case 1:21-cv-10865-NMG, D27-1).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Complaint, filed May 25, 2021, 197 pages (case 1:21-cv-10865-NMG, D1).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. Notice of Appearance, filed on Janurary 12, 2023, 2 pages (case 1:21-cv-10865-NMG, D131).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. Plaintiffs' Responsive Claim Construction Brief, filed on Dec. 8, 2022, 29 pages (Case 1:21-cv-10865-NMG, D126).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. Report on the Filing or Determination of an Action Regarding a Patent or Trademark, AO 120, filed on May 25, 2021, 2 pages (case 1:21-cv-10865-NMG, D2).
U.S. Appl. No. 61/222,428, filed Jul. 2, 2009, 27 pages.

(56) References Cited

OTHER PUBLICATIONS

Sweeney, "k-Anonymity: A Model for Protecting Privacy," International Journal of Uncertainty, Puzziness and Knowledge-Based Systems, May 2002, 10(5);557-570.
U.S. Appl. No. 14/082,433, filed Nov. 18, 2013.
U.S. Appl. No. 15/136,318, filed Apr. 22, 2016.
U.S. Appl. No. 15/606,265, filed May 26, 2017.
U.S. Appl. No. 15/939,727, filed Mar. 29. 2018.
U.S. Appl. No. 12/827,745, filed Jun. 30, 2010.
U.S. Appl. No. 14/732,358, filed Jun. 5, 2015.
U.S. Appl. No. 16/131,094, filed Sep. 14, 2018.
U.S. Appl. No. 17/060,558, filed Oct. 1, 2020.

* cited by examiner

USING DE-IDENTIFIED HEALTHCARE DATA TO EVALUATE POST-HEALTHCARE FACILITY ENCOUNTER TREATMENT OUTCOMES

CLAIM OF PRIORITY

This application is a continuation of and claims priority under 35 U.S.C. § 120 to U.S. application Ser. No. 15/939,727, filed Mar. 29, 2018, which is a continuation of U.S. application Ser. No. 15/606,265, filed May 26, 2017 (now U.S. Pat. No. 9,965,651 issued on May 8, 2018), which is a continuation of U.S. application Ser. No. 15/136,318, filed Apr. 22, 2016 (now U.S. Pat. No. 9,665,685 issued on May 30, 2017), which is a continuation of U.S. application Ser. No. 14/082,433, filed Nov. 18, 2013 (now U.S. Pat. No. 9,323,892 issued on Apr. 26, 2016), which is a continuation-in-part application of U.S. application Ser. No. 12/827,745, filed Jun. 30, 2010, (now U.S. Pat. No. 9,118,641 issued on Aug. 25, 2015), which claims priority under 35 U.S.C. § 119(e) to U.S. provisional application No. 61/222,428, filed on Jul. 1, 2009; U.S. application Ser. No. 14/082,433, filed Nov. 18, 2013, also claims priority under 35 USC § 119(e) to U.S. Patent Application Ser. No. 61/729,207, filed on Nov. 21, 2012; the entire contents of each are hereby incorporated by reference.

BACKGROUND

The present disclosure relates to processing and transmitting personal data, the dissemination of which is restricted by federal law.

Due to federal privacy laws and the inconsistency of electronic medical record deployments, healthcare facilities (e.g., hospitals, nursing homes, residential mental health facilities, prison medical wards) are often unable to obtain information about health care services patients receive before or after healthcare facility encounters. Having access to these data may allow healthcare facilities to better serve patients. Gaining an understanding of care that occurs in the outpatient setting is needed to evaluate potential for changes in the process of inpatient care. Not having this information may lead to unrecognized suboptimal care and ultimately to healthcare facility readmission for which the healthcare facility may be held accountable. Outpatient healthcare providers such as pharmacies and physicians generate private healthcare data about patients, including medical and prescription drug data, and administrative healthcare claims data. Data that associates patient identity with health information is known as protected health information (PHI). Healthcare providers can store protected health information in electronic databases for future use in patient care and insurance claims processing. Healthcare facilities could identify changes in the process of care provided (e.g., patient and provider education, adherence follow-up) by having information on trends in health care utilization before and after health care facility encounters. Federal privacy laws, however, make obtaining this information a cumbersome process which would add considerable expense to operations.

SUMMARY

The systems and techniques described here relate to de-identifying patient identities from healthcare facility encounters and retrieving information from pre or post encounter activity.

In one aspect, a computer-implemented method includes producing medical information from a set of private data representing pre or post-encounter characteristics of the individuals, where the individuals have had an encounter with a healthcare facility. The identity of the individuals is unattainable from the produced medical information. The method includes using the produced medical information to report the pre or post-encounter characteristics for the group.

Implementations may include any of all of the following features. Producing medical information that characterizes the group of encounters may include producing a request token for each individual included in the group of encounters. Producing such a request token for each individual may include encrypting respective data that identifies each individual. Producing medical information that characterizes the group of encounters may include comparing the request tokens to tokens associated with the medical information to be produced. The tokens associated with the medical information to be produced and the request tokens may be similarly encrypted. Producing medical information that characterizes the group of encounters may include determining if the comparison provides at least a minimum number of matches. Producing medical information that characterizes the group may include requesting a predefined portion of the medical information. Additionally, producing medical information that characterizes the group may include determining if the group includes at least a minimum number of individuals. The private data may represent medical information associated with pre or post-encounter medical activity for the individuals within the group. The private data may be obtained from pharmacies or other medical care providers.

In another aspect a system includes an encryption server for producing a request token for each individual included in a group identified in a request for medical information that characterizes the group consisting of individuals who had an encounter with a healthcare facility. The system may also include a data server for producing the medical information that characterizes the group from a set of private data representing pre or post-encounter characteristics of the individuals. The identity of the individuals is unattainable from the produced medical information. The data server is also configured to provide the produced medical information to report the characteristics of the group of encounters.

Implementations may include any of all of the following features. The data server may provide a request token for each individual included in the group of encounters to produce the medical information that characterizes the group of encounters. The request token for each individual may represent encrypted data that identifies the corresponding individual. The data server may be configured to compare the request tokens to tokens associated with the medical information to be produced. The tokens associated with the medical information to be produced and the request tokens may be similarly encrypted. The data server may be configured to determine if the comparison provides at least a minimum number of matches. The request may represent a predefined portion of information to use for producing the medical information that characterizes the group of encounters. The encryption server may be configured to determine if the group includes at least a minimum number of individuals. The private data may represent medical information associated with pre or post-encounter medical activity of the individuals within the group. The private data may be obtained from pharmacies or other medical care providers.

In another aspect, one or more computer readable media storing instructions that are executable by a processing device, and upon such execution cause the processing device to perform operations that include producing medical information that characterizes a group of individuals from a set of private data representing pre or post encounter characteristics of the individuals. The individuals have had an encounter with a healthcare facility. The identity of the individuals is unattainable from the produced medical information. The operations also include providing the produced medical information to report the characteristics of the group.

Implementations may include any of all of the following features. Producing medical information that characterizes the group may include producing a request token for each individual included in the group. Producing such a request token for each individual may include encrypting respective data that identifies each individual. Producing medical information that characterizes the group of encounters may include comparing the request tokens to tokens associated with the medical information to be produced. The tokens associated with the medical information to be produced and the request tokens may be similarly encrypted. Producing medical information that characterizes the group may include determining if the comparison provides at least a minimum number of matches. Producing medical information that characterizes the group may include requesting a predefined portion of the information. Additionally, producing medical information that characterizes the group of encounters may include determining if the group includes at least a minimum number of individuals. The private data may represent medical information associated with pre or post-encounter medical activity of the individuals of the group of encounters. The private data may be obtained from pharmacies or other medical care providers.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
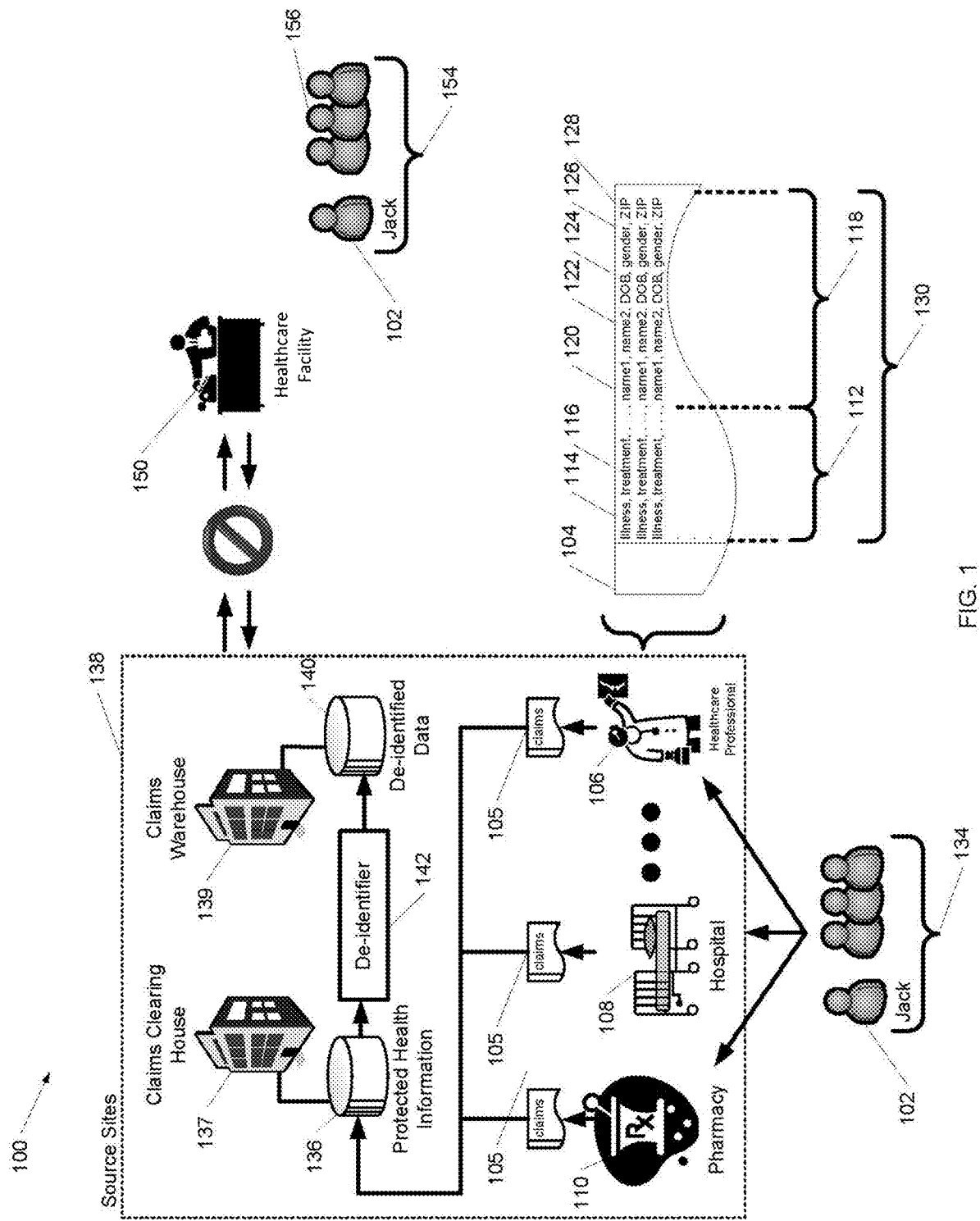
FIG. 1 illustrates exemplary circumstances in which protected health information is stored by healthcare providers, claims clearing houses, and other source sites, and requested by a hospital.

Referring to FIG. 1, when a doctor treats Jack 102 for high blood pressure, a surgeon removes Jack's gallstones, and a pharmacist fills Jack's prescription for insulin, Jack leaves a trail of electronic records 104 with healthcare professionals (e.g., healthcare professional 106), in their offices (e.g., doctor's office, nurse's station, etc.), in healthcare facilities (e.g., a hospital 108, a pharmacy 110, a nursing home, etc.) and the like. The electronic records 104 contain medical data 112 about Jack, for example his illnesses 114 and treatments 116. Each piece of medical data 112 is associated with personally identifiable information 118 that identifies Jack and distinguishes him from all other patients, such as his first name 120, last name 122, date of birth 124, gender 126, and zip code 128. Together, the pieces of medical data 112 and the personally identifiable information 118 make up Jack's protected health information (PHI) 130.

Each of Jack's healthcare providers may submit health insurance claims 105 containing PHI 130, as well as additional PHI 130, to a claims clearing house 137. The claims clearing house 137 may store the PHI 130 of many patients 134, including Jack, in a PHI database 136. A de-identifier 142 can process the PHI 130 to generate irreversibly de-identified data 140 by removing all personally identifiable information 118 or otherwise transforming the PHI 130 so that it cannot be associated with a particular person. A claims warehouse 139 stores de-identified data 140 about many patients 134. Claims clearing houses 137 and claims warehouses 139 are optimized for retrieving and providing PHI 136 and de-identified data 140 for use in further processing, but health care providers such as healthcare professionals 106 and pharmacies 110 may also serve as source sites 138 for de-identified data in a distributed system.

By searching for Jack's personally identifiable information 118 in its electronic records 104, the pharmacy 110 is able to look up the various drugs in Jack's PHI 130 and, for example, check for bad interactions among them. Jack does not object to this use of his PHI 130 because it improves the quality of his healthcare. On the other hand, Jack would object to the pharmacy 110 giving his PHI 130 to third parties without his permission because that would disclose personal, private information about him that Jack's potential employers, for example, might use to discriminate against him.

Federal laws, such as the Health Insurance Portability and Accountability Act (HIPAA), protect Jack by prohibiting the source sites 138 possessing Jack's PHI 130 from releasing it to third parties without Jack's permission. Under HIPAA, the source sites 138 can release only irreversibly de-identified data 140 without Jack's permission.

A healthcare facility, for example a hospital 150, may be interested in outpatient medical information contained in Jack's PHI 130 that occurs post-discharge. Since the hospital may not have access to post discharge medical information it may not have the knowledge to fully understand the potential risk of rehospitalizations or other medical events for a group 154. In that case, the hospital 150 would like to use the PHI 136 from the group 154 to assess the risk of rehospitalization or other medical events. The hospital can use this information to make adjustments to treatments and improve the quality of care. Unfortunately, the group 154 may also be too large for the hospital 150 to practically obtain permission from each person in the group, without which HIPAA prohibits the healthcare providers 138 from releasing the PHI 136 to the hospital 150 for care not related to the hospitalization. Practically speaking, even when hospitals have the authority to obtain the requested data they may not have a mechanism for doing so. The de-identified data 140, which the healthcare providers or other source sites 138 could release without permission, is not useful to the hospital 150 because the hospital has no way to know whether it corresponds to the people in the group 154. With no way to obtain pre and post hospitalization medical data for the group, the hospital 150 cannot determine post discharge medical events for the group.

Figure 2:
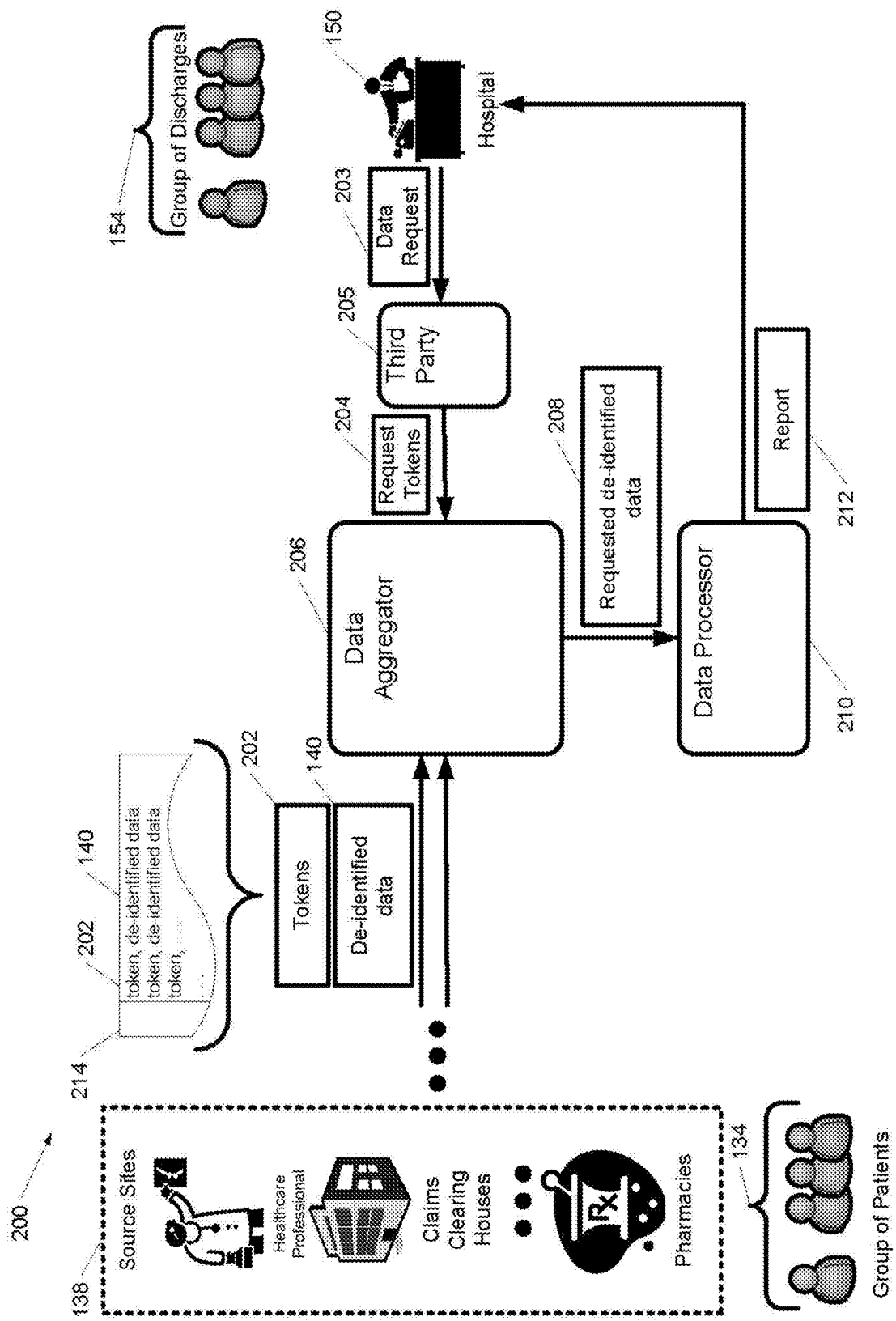
FIG. 2 illustrates an exemplary method and system that enables a hospital to obtain medical information about a group of people without violating the privacy of persons in the group.

Referring to FIG. 2, to provide the hospital 150 with the pre and post hospitalization medical data necessary to generate the post discharge report for the group 154, without revealing the protected health information of persons in the group 154, the exemplary system 200 associates unique tokens 202 with the irreversibly de-identified data 140. The tokens 202 correspond to persons treated by healthcare providers but do not reveal the identities of the treated individuals. The hospital 150 can send a data request 203 to a third party 205, who in turn can generate request tokens 204, one for each person in the group 154. The third party 205 can send the request tokens 204 to a data aggregator 206. The data aggregator 206 stores de-identified data 140 and associated tokens 202. By searching for the request tokens 204 among the stored tokens 202, the data aggregator 206 can process the de-identified data to generate requested de-identified data 208 that corresponds to the group 154. A data processor 210 can process the requested de-identified data 208 to generate a report 212 containing metrics such as medication utilization reports that are useful to the hospital 150 in assessing the overall post discharge health status of the group 154.

By using the tokens 202 and request tokens 204, no parties other than the authorized source sites 138 can associate de-identified data 140 with the identity of any person in the group of patients 134 or discharges (e.g., the group 154). The hospital 150 requesting the report 212 can never receive data associated with individuals. Further, the information in the report 212 may be processed into metrics that characterize a large group and cannot be used to infer information about individuals. De-identified data records may be provided to the data processor 210 (e.g., a third party data processor), but that third party may not have access to any personally identifiable information 118 about the group 154. Nor may any party with access to the de-identified data 140, other than the healthcare providers 138, also have access to the de-identifier 142. These features of the system 200 maintain the privacy of the protected health information 130.

While we describe a system in which a hospital 150 needs to estimate the post discharge health status of a group of discharges, the system 200 can work for applications in which information characterizing a group needs to be generated from the private data of group members. In one arrangement, the system may implement Microsoft Windows-based computers in connection with internet-based components. However, other implementations may use other types of components that support the processing of pre and post hospitalization medical data from healthcare databases.

While the hospital 150 is referred to as a location interested in the post discharge health status of a group of discharges, one or more other types of healthcare facilities may utilize the techniques and methodologies described herein. Such healthcare facilities may include dialysis centers, specialty clinics, retirement homes, rehabilitation centers, or other types of entities where post encounter follow up may be of interest.

Figure 3:
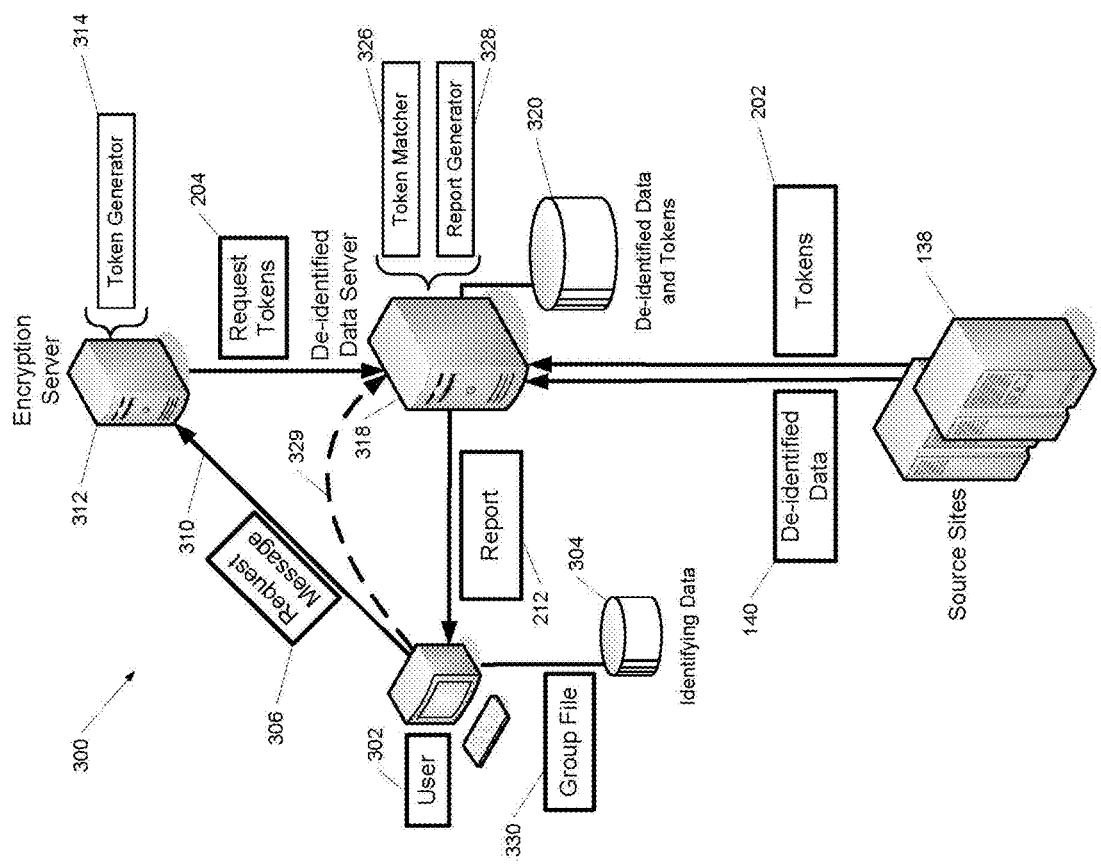
FIG. 3 illustrates an exemplary system incorporating an encryption server and a de-identified data server to enable a user who is not permitted to obtain the private data of a group of individuals who have been discharged from a hospital to instead obtain a report that characterizes the group of discharges as a whole.
Figure 4:
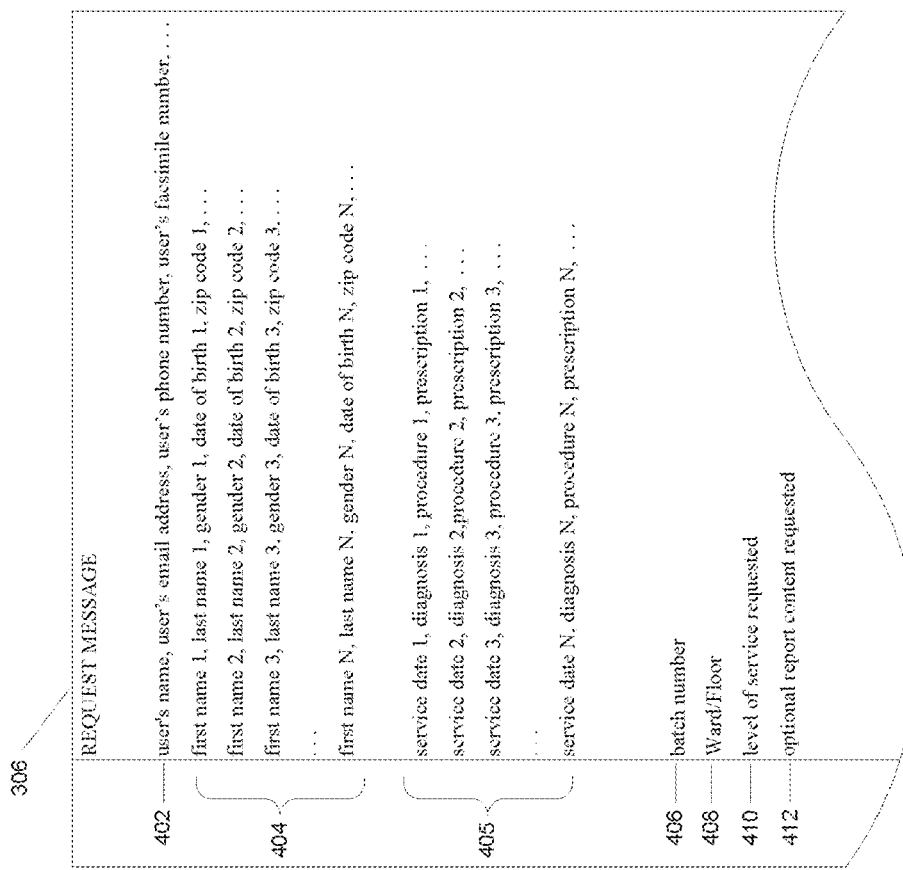
FIG. 4 illustrates an exemplary message requesting de-identified data about a group of discharges.

Referring to FIG. 3, in an exemplary system 300, a user 302 specifies a group of people using identifying data for each group member. Referring briefly to FIG. 4, an exemplary set of identifying data 404 is illustrated. Returning to FIG. 3, the user may obtain the personally identifiable information from a database 304 by retrieving it in the form of a group file 330. The user 302 generates a request message 306, which may be a computer file, which uniquely identifies each member of the group using the identifying data 304. Typically, the group contains at least a minimum number of unique members. A request message 306 may be generated at a remote computer operated by the user 302.

The request message 306 contains a set of identifying data 404 (see FIG. 4) for each group member, as well as data that identifies a user 402 (see FIG. 4), such as the user's name, email address, phone number and facsimile number, and a batch number 406 that identifies the request. The group members' identifying data 404 (see FIG. 4) may include first name, last name, date of birth, gender, and zip code as well as other identifiers, such as social security number, that may be added to ensure that members are uniquely identified. In some examples, fewer identifiers may be used. The request message 306 may also include optional indications that the user 302 requests a particular type of report 212 or requests additional processing to enhance the value of the report. The request message may also contain additional non-identified (not containing any personally identifiable information) data 405 to be used by a report generator 328. These additional non-identified data 405 will be encrypted upon submission allowing access to only a report generator 328. Alternatively, the additional data 405 may be passed directly to the report generator 328 as shown by dotted line 329. These non-identified data 405 may include service dates, diagnosis information, or other pre-encounter and/or post-encounter details.

The request message 306 is sent over a communications network 310 (e.g., the Internet, a LAN, etc.) to an encryption server 312. If the request message 306 contains a minimum number of unique group members, the encryption server 312 creates a unique token, or identifier, for each person in the message 306. The encryption server creates each token by applying a token generator 314 that encrypts the personally identifiable information of each group member and passes the pre-encrypted non-identified data through the system to a report writer. The set of tokens corresponding to all the group members constitutes a batch of request tokens 204. The minimum number of group members, for example ten, is chosen to make it effectively impossible to associate individual group members with individual tokens in the batch of request tokens 204.

The encryption server 312 provides the request tokens 204 to the de-identified data server 318. The de-identified data server 318 stores records of de-identified data and corresponding tokens 320 obtained from source sites 138 such as pharmacies, healthcare professionals, rehabilitation centers, and electronic claims clearing houses. Other sources of data can include prison records, arrest records, the national death index or other death records, medical laboratories, dialysis centers, nursing homes, radiology providers, potentially military records, employment records, financial records, or DMV records. Each token obtained from the source sites 138 may have been created using the same token generator 314 used by the encryption server 312, or using any other means that generates the identical token for the same personally identifiable information.

For example, a pharmacy tracks the prescription histories of the patients being served. De-identified prescription histories and corresponding tokens are sent to the de-identified data server 318. At the request of a user 302, such as a hospital, the encryption server 312 generates tokens identical to the patients' tokens using the same personally identifiable information. A unique token corresponding to the same personally identifiable information permits the pharmacy and the hospital to refer to the same anonymous people without the hospital ever associating protected health information with a particular person. To produce tokens and request tokens, one or more encryption techniques may be utilized, for example, hash functions and other methodologies may be implemented.

A token matcher 326, executed by the de-identified data server 318, performs a look-up in the de-identified database 320 to find all tokens in the database that match the tokens sent from the encryption server 312. All available data for matched tokens, the requested de-identified data 208, is retrieved for use in the report generator 328. The de-identified data may include, for example, prescription data, medical claims, and hospital claims. The de-identified data server 318 or the data processor 210 may use the report generator 328 to process the requested de-identified data 208 in a way that leaves it irreversibly de-identified. An example of such processing is an algorithm that transforms the data into a post discharge health status assessment. The report generator formats the processed data into an electronic or hardcopy report 212 that is returned to the user.

While the report 212 is described as generated on a computer system, it may also be generated in part or entirely outside the computer system. For example, the report 212 could be conveyed to the user via regular mail or other similar technique. In particular, the report may be generated and printed at the site of the de-identified data server 318 and subsequently communicated to the user 302 without using the computer network. The report generator 328 may also reside in the data processor 210 separate from the de-identified data server 318.

In one arrangement, once the relevant information and options have been selected, the user 302 submits the request by clicking a submit button. The request message 306 may be encrypted prior to being transmitted over a computer network 310. At the encryption server 312, the request message 306 is unencrypted and stored. The encryption server 312 may send an optional confirmation message to the user 302. The confirmation message may include the time and date that the message was received, and may indicate the service level and options selected by the user 302.

Referring to FIG. 4, the user 302 can input the user's identifying information 402, including name, email address, phone number and/or facsimile number, in the first record, or set of fields, of the request message 306. The user can then input the personally identifiable information 404 for each of the group members, including first name, last name, gender, date of birth, and zip code. The user may also input additional data 405 such as service dates, diagnosis information, or other encounter details that will be rendered non-identified and encrypted upon submission. Equivalently, the user can incorporate the group file 330 into the request message 306. Information about the ward 408 from which the group was discharged, or other purpose for which the report 212 is being requested may also be included in the request message 306. The format of the request message 306 may be adjusted based on the user's 302 needs.

The request message 306 may also include information about the level of service 410 requested by the user 302, for example the quantity, quality or type of information. A first level of service may request up to six months of pre and post hospitalization medical data; a second level may request up to twelve months of data; and a third level may request a two year pre and post hospitalization medical data. Alternatively, instead of providing the user 302 with a variety of service level options 410, the system 300 may simply retrieve all of the pre and post hospitalization medical data available for the group.

The user 302 may also request additional, optional information 412. For example, the user 302 may request information regarding the drug categories and drug indications associated with the drugs in the de-identified data. Drug indications include the medical conditions associated with each drug. Drug categories include the type of drug. This data can be passed to the data processor 210 to include in the report 212. Alternatively, this data may be returned as part of every report 212.

Figure 5:
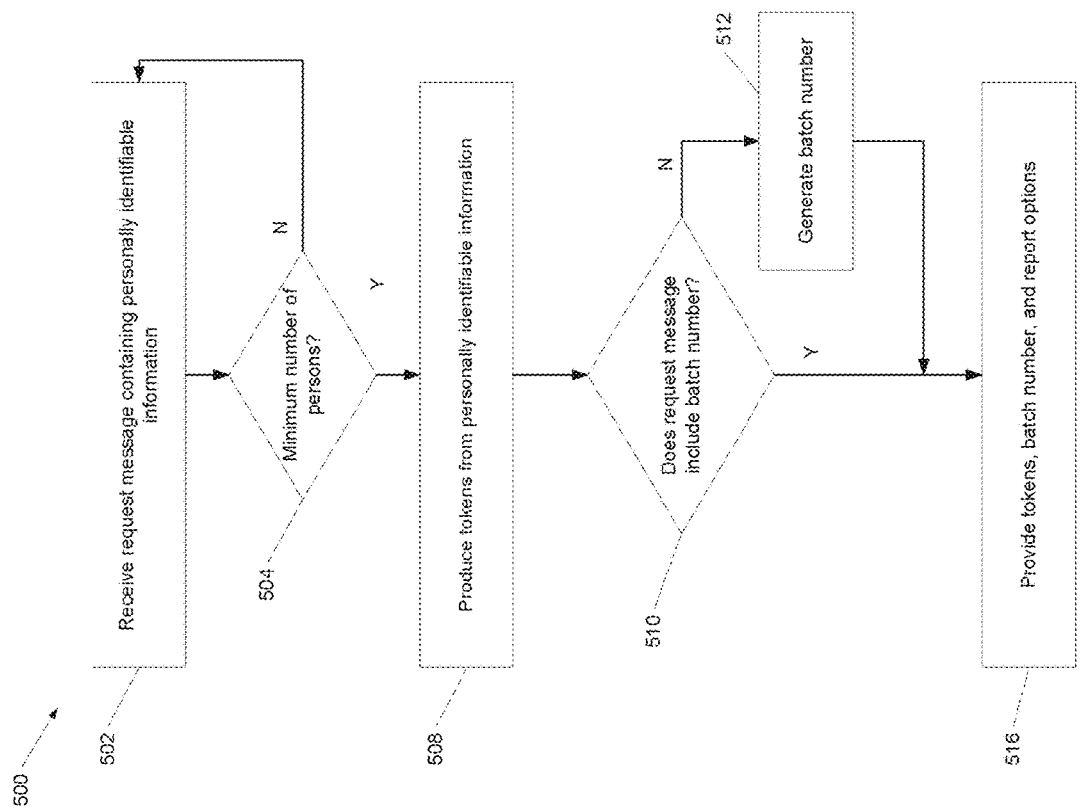
FIG. 5 is a flowchart that represents exemplary operations of a token generator.

Referring to FIG. 5, a flowchart 500 represents a particular arrangement of operations of a token generator (e.g., the token generator 314 shown in FIG. 3). Operations include receiving 502 the request message (e.g., request message 306) containing the personally identifiable information of each person in the group (e.g., such as the group 154 shown in FIG. 1). Upon receiving the request message, operations may also include determining 504 whether the message includes the minimum number of persons. If the message does not include the minimum number of persons, the token generator returns to receive 502 a request message. A limit on the minimum number of persons ensures that a report (e.g., the report 212) covers enough people such that it is difficult (if not impossible) to infer any association between particular persons and the information in the report. If the message does include the minimum number of people, operations of the token generator include producing 508 tokens from the identifying data of each person. Producing the tokens may include applying an encryption algorithm to the identifying data of each person. The tokens uniquely identify each person in the group 154.

Operations also include determining 510 if the request message includes a batch number. If the message does not include a batch number, operations include generating 512 a batch number. Operations also include providing 516 the tokens, batch number and report options. The individual tokens are placed in a batch file and may be encrypted before being transmitted over the network.

Each batch file of request tokens 204 also specifies the information needed for the report 212. The request tokens are transmitted to the de-identified data server 318, unencrypted and processed using rules for searching, matching, and retrieving healthcare data.

Figure 6:
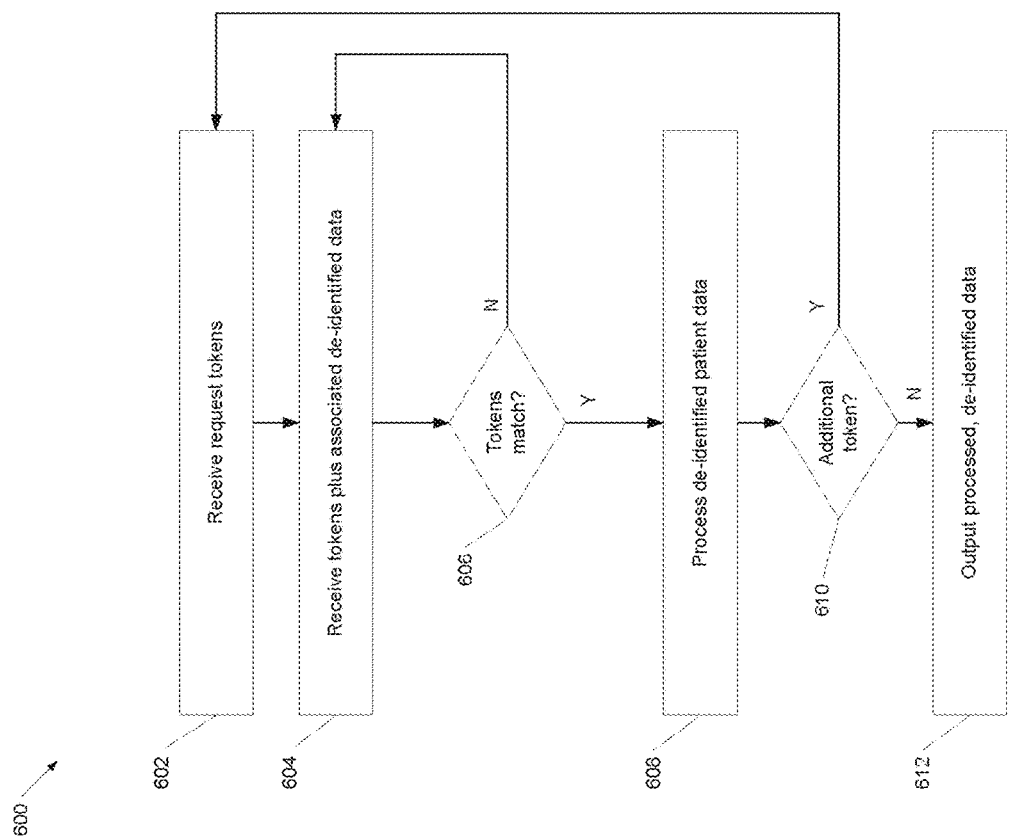
FIG. 6 is a flowchart that represents exemplary operations of a token matcher.

Referring to FIG. 6, a flowchart 600 represents a particular arrangement of operations of a token matcher (e.g., the token matcher 326 shown in FIG. 3). Operations include receiving 602 request tokens (e.g., such as the request tokens 204 shown in FIG. 2). Operations may also include receiving 604 a token (e.g., such as the token 202) and associated de-identified data (e.g., such as the de-identified data 140), typically from source sites (e.g., such as the source site 138 shown in FIG. 1). Upon receiving a request token, de-identified data and a token, operations include determining 606 whether the request token matches the token. If no match is found, operations include returning to receive 604 more tokens and de-identified data. If a match is found, operations include processing 608 the de-identified data. Processing may include storage for later retrieval. In some arrangements, operations may also include determining whether a minimum number of matches has been detected. If such a minimum number of matches has not occurred in comparing the request tokens and the tokens, action may be taken (e.g., pause or restart processing) until the predefined number of matches has been detected (e.g., so as not to increase the probability of one or more individuals being identified by a process of elimination).

In addition to determining that a minimum number of matches has been found operations may also include processing of other privacy-preserving rules. For example, a rule may not allow the same user 302 (e.g., hospital 150) to submit more than one request message 306 containing substantially the same identifying data 404 within a defined period of time, e.g., six months. Identifying substantially the same identifying data 404 from a user 302 may involve comparing the identifying data 404 from different stored request messages 306 and checking that at least a minimum variation exists in the request messages 306. For example, this may involve checking that the identifying data 404 for at least five patients does not match the identifying data 404 for any previous search request 306 by the user 302. Especially when combined with the size requirements and less than 100% capture rate, such rules greatly reduce the possibility of identifying any one person's data.

The de-identified data (e.g., such as the de-identified data 140) may include a list of drugs prescribed over the requested period for the members of the group (e.g., such as the group 154). The list of drugs prescribed may include the drug name, form, strength, days supplied, and date dispensed. The de-identified data could also include data from other sources such as those listed above, and include diagnosis, procedures, prison release date, date of death, date of arrest, etc. As part of processing 608 the de-identified data, operations may include determining the drug category and drug indications for each drug prescribed. Operations may also include accessing a database relating the drug category and indications to each possible drug. The database may be maintained within the de-identified data server 318 database, or may be accessed on a remote server maintained by a third party.

Upon processing the de-identified data, operations also include determining 610 if additional tokens remain in the batch of request tokens (e.g., such as the request tokens 204). If additional tokens remain, operations include receiving 602 more request tokens. If there are no additional request tokens, operations may include outputting 612 the processed, de-identified data.

Operations may also include providing the number of tokens submitted, the number matched, and the overall match rate. The collected data covers the interval of historical data according to the level of service requested (e.g., as represented by the level of service 410 in FIG. 4). De-identified diagnosis and procedures data may also be included from administrative medical claims from a doctor's office (e.g., office 106) or a healthcare facility (e.g., the hospital 108).

In addition to accessing and incorporating drug indication information for each drug prescribed to persons in the group (e.g., such as group 154), operations may include further processing of the requested de-identified data. For instance, operations may include determining the probability that a particular drug indicates a particular condition. In this example, in addition to providing the possible indications, the requested de-identified data would include the likelihood that anonymous individuals associated with the request tokens (e.g., such as request tokens 204) have each of the conditions indicated by the prescribed drugs. Operations may also include using expert rule systems to provide health status information based on the prescription drug medical data. Alternatively, operations may include using diagnosis codes from medical claims data to assess health status. In some arrangements, operations may also include integrating the de-identified data with the non-identified data 405.

The requested de-identified data 208 may be sent for further processing to a third party data processor (e.g., data processor 210) who may apply proprietary algorithms, modify the data format, or generate additional reports, provided that no re-identifiable information is transmitted to the user 302. Third parties may not have access to the request message 306 and the group file 330 so that no association may be inferred between the de-identified data 140 and particular persons in the group 154.

In some implementations, the report 212 can include analysis results. The analysis results can include statistical analyses, correlations of varying post-discharge characteristics, comorbidity rates, or other metadata. The analysis results can be determined by the third party data processor. The analysis results can be generated automatically, or by human intervention. For example, in addition to the report 212, a human analyst can respond to the user 302 with custom analysis relating to the user's 302 request message 306.

The report 212 provides the hospital 150 with information for making an informed decision about the relationship between the hospitalization and the health status of the group of discharges. Hospitals could identify changes in the process of care provided during or after the hospitalization by having information on trends in outpatient health care utilization. In particular, the hospital 150 may change internal policies including discharge instructions, structure of care, process of care, or other relevant operating procedures based on the information in the report 212. Patterns from multiple reports over time may be used to determine which actions to take, if any. The report 212 may be used alone to make decisions about the health status of the group 154, or may simply indicate that additional investigation is needed.

In some implementations, all reports 212 can be saved and archived by the system 200. Data on the saved reports 212 can be made available to the hospital 150. For example, a hospital 150 may query the system 200 about a group 154 of patients sharing a characteristic, and deliver a report for the group as well as a second report. The second group could include, for example, comparative data for all patients discharged from the hospital.

Figure 7:
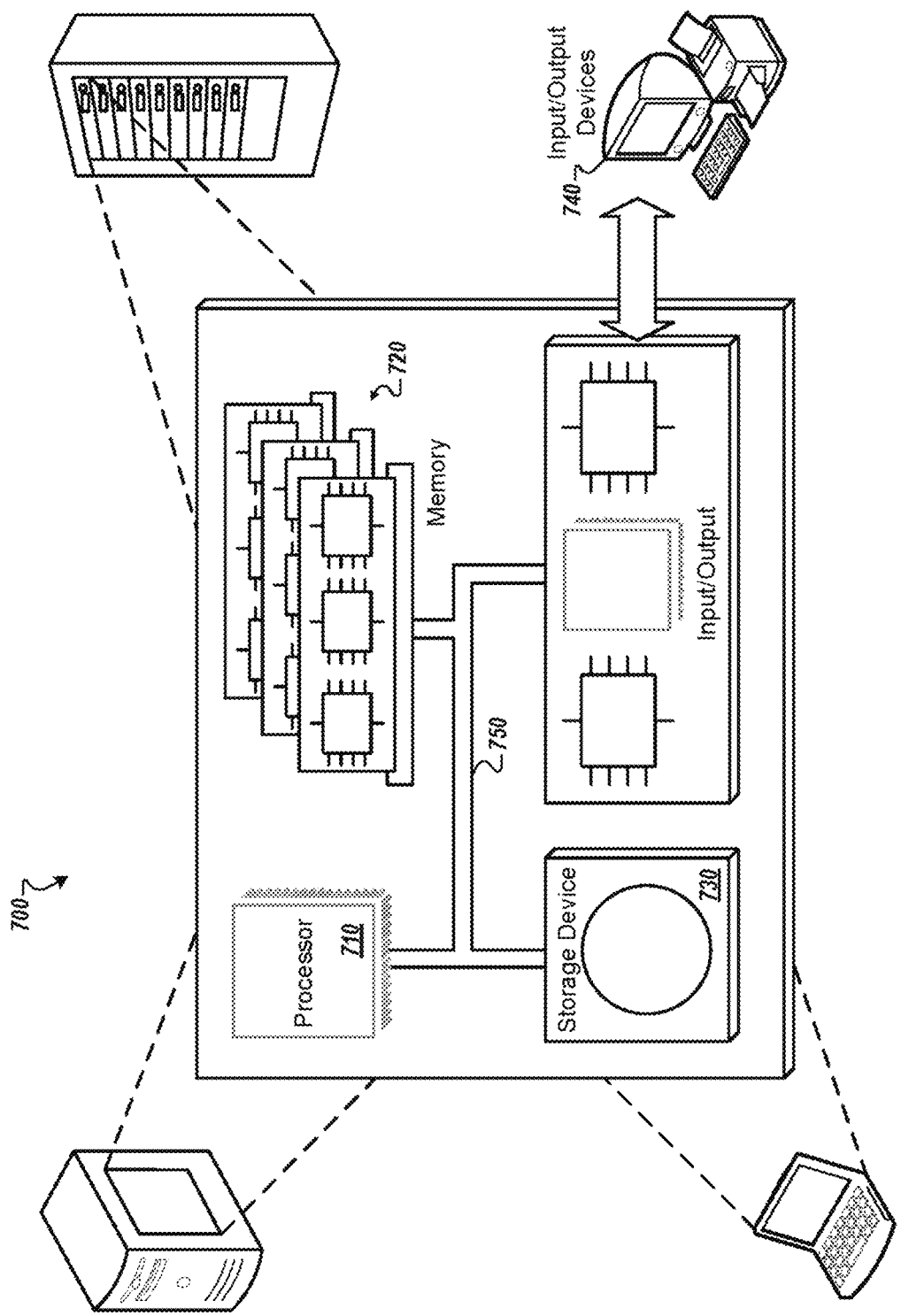
FIG. 7 represents a computer system and related components.

FIG. 7 is a schematic diagram of a generic computer system 700. The system 700 can be used for the operations described in association with any of the computer-implemented methods described previously, according to one implementation. The system 700 includes a processor 710, a memory 720, a storage device 730, and an input/output device 740. Each of the components 710, 720, 730, and 740 are interconnected using a system bus 750. The processor 710 is capable of processing instructions for execution within the system 700. In one implementation, the processor 710 is a single-threaded processor. In another implementation, the processor 710 is a multi-threaded processor. The processor 710 is capable of processing instructions stored in the memory 720 or on the storage device 730 to display graphical information for a user interface on the input/output device 740.

The memory 720 stores information within the system 700. In some implementations, the memory 720 is a computer-readable medium. The memory 720 is a volatile memory unit in some implementations and is a non-volatile memory unit in other implementations.

The storage device 730 is capable of providing mass storage for the system 700. In one implementation, the storage device 730 is a computer-readable medium. In various different implementations, the storage device 730 may be a floppy disk device, a hard disk device, an optical disk device, or a tape device.

The input/output device 740 provides input/output operations for the system 700. In one implementation, the input/output device 740 includes a keyboard and/or pointing device. In another implementation, the input/output device 740 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, e.g., in a machine-readable storage device, for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network, such as the described one. The relationship of client and server arises by virtue of computer programs running on the respective computers and having a client-server relationship to each other.

A number of implementations have been described. Nevertheless, it will be understood that various modifications may be made without departing from the spirit and scope of the following claims.

What is claimed is:

1. A computer-implemented method comprising:
receiving, at an encryption server, a request from a user device for medical information that characterizes a first group composed of multiple individuals, wherein at least one of the multiple individuals has not authorized provision of personal medical information at any time;
determining that the first group comprises at least a defined minimum number of individuals;
subsequent to determining that the first group comprises at least the defined minimum number of individuals, producing, by a processor of the encryption server, one or more request tokens from a first set of personally identifiable information associated with the multiple individuals, wherein the first set of personally identifiable information is provided in the request and wherein each of the one or more request tokens is unique to a corresponding individual of the multiple individuals;
comparing the request tokens to tokens generated independently of the request tokens to find matching tokens,
wherein the independently generated tokens are generated from a second set of personally identifiable information associated with a second group of individuals, each of the independently generated tokens being unique to a corresponding individual from the second group and associated with de-identified medical information about the corresponding individual from the second group, the de-identified medical information representing pre- or post-encounter characteristics of the corresponding individual from the second group, and
wherein at least a portion of the independently generated tokens match at least a portion of the request tokens if the portion of the independently generated tokens and the portion of the request tokens correspond to the same individuals;
determining that at least a defined minimum number of matches have been found;
subsequent to determining that at least the defined minimum number of matches have been found, producing the de-identified medical information associated with the independently generated tokens that were matched to the request tokens; and
providing the produced de-identified medical information to report characteristics of the first group.

2. The computer-implemented method of claim 1, wherein the provided de-identified medical information is provided in conformity with the Health Insurance Portability and Accountability Act (HIPAA).

3. The computer-implemented method of claim 1, in which producing the one or more request tokens includes encrypting at least a portion of the first set of personally identifiable information associated with the multiple individuals.

4. The computer-implemented method of claim 1, in which the independently generated tokens and the request tokens are similarly encrypted.

5. The computer-implemented method of claim 1, wherein producing the one or more request tokens comprises producing the one or more request tokens in a reproducible manner.

6. A system comprising:
a computing device comprising:
a memory configured to store instructions; and
a processor to execute the instructions to perform operations comprising:
receiving a request from a user device for medical information that characterizes a first group composed of multiple individuals, wherein at least one of the multiple individuals has not authorized provision of personal medical information at any time;
determining that the first group comprises at least a defined minimum number of individuals;
subsequent to determining that the first group comprises at least the defined minimum number of individuals, producing one or more request tokens from a first set of personally identifiable information associated with the multiple individuals, wherein the first set of personally identifiable information is provided in the request and wherein each of the one or more request tokens is unique to a corresponding individual of the multiple individuals;
comparing the request tokens to tokens generated independently of the request tokens to find matching tokens,
wherein the independently generated tokens are generated from a second set of personally identifiable information associated with a second group of individuals, each of the independently generated tokens being unique to a corresponding individual from the second group and associated with de-identified medical information about the corresponding individual from the second group, the de-identified medical information representing pre- or post-encounter characteristics of the corresponding individual from the second group, and
wherein at least a portion of the independently generated tokens match at least a portion of the request tokens if the portion of the independently generated tokens and the portion of the request tokens correspond to the same individuals;
determining that at least a defined minimum number of matches have been found;
subsequent to determining that at least the defined minimum number of matches have been found, producing the de-identified medical information associated with the independently generated tokens that were matched to the request tokens; and
providing the produced de-identified medical information to report characteristics of the first group.

7. The system of claim 6, wherein the provided de-identified medical information is provided in conformity with the Health Insurance Portability and Accountability Act (HIPAA).

8. The system of claim 6, in which producing the one or more request tokens includes encrypting at least a portion of the first set of personally identifiable information associated with the multiple individuals.

9. The system of claim 6, in which the independently generated tokens and the request tokens are similarly encrypted.

10. The system of claim 6, wherein producing the one or more request tokens comprises producing the one or more request tokens in a reproducible manner.

11. One or more computer readable storage devices storing instructions that are executable by a processing device, and upon such execution cause the processing device to perform operations comprising:
receiving, at an encryption server, a request from a user device for medical information that characterizes a first group composed of multiple individuals, wherein at least one of the multiple individuals has not authorized provision of personal medical information at any time;
determining that the first group comprises at least a defined minimum number of individuals;
subsequent to determining that the first group comprises at least the defined minimum number of individuals, producing, by a processor of the encryption server, one or more request tokens from a first set of personally identifiable information associated with the multiple individuals, wherein the first set of personally identifiable information is provided in the request and wherein each of the one or more request tokens is unique to a corresponding individual of the multiple individuals;
comparing the request tokens to tokens generated independently of the request tokens to find matching tokens,
wherein the independently generated tokens are generated from a second set of personally identifiable information associated with a second group of individuals, each of the independently generated tokens being unique to a corresponding individual from the second group and associated with de-identified medical information about the corresponding individual from the second group, the de-identified medical information representing pre- or post-encounter characteristics of the corresponding individual from the second group, and
wherein at least a portion of the independently generated tokens match at least a portion of the request tokens if the portion of the independently generated tokens and the portion of the request tokens correspond to the same individuals;
determining that at least a defined minimum number of matches have been found;
subsequent to determining that at least the defined minimum number of matches have been found, producing the de-identified medical information associated with the independently generated tokens that were matched to the request tokens; and
providing the produced de-identified medical information to report characteristics of the first group.

12. The computer readable storage devices of claim 11, wherein the provided de-identified medical information is provided in conformity with the Health Insurance Portability and Accountability Act (HIPAA).

13. The computer readable storage devices of claim 11, in which producing the one or more request tokens includes encrypting at least a portion of the first set of personally identifiable information associated with the multiple individuals.

14. The computer readable storage devices of claim 11, in which the independently generated tokens and the request tokens are similarly encrypted.

15. The computer readable storage devices of claim 11, wherein producing the one or more request tokens comprises producing the one or more request tokens in a reproducible manner.

\* \* \* \* \*